(12) United States Patent
Mauro et al.

(10) Patent No.: US 8,785,611 B2
(45) Date of Patent: Jul. 22, 2014

(54) COMPOSITIONS AND METHODS RELATED TO MRNA TRANSLATIONAL ENHANCER ELEMENTS

(75) Inventors: Vincent P. Mauro, San Diego, CA (US); Gerald M. Edelman, San Diego, CA (US); Wei Zhou, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 236 days.

(21) Appl. No.: 12/316,581

(22) Filed: Dec. 11, 2008

(65) Prior Publication Data

US 2009/0226470 A1 Sep. 10, 2009

Related U.S. Application Data

(60) Provisional application No. 61/007,440, filed on Dec. 11, 2007.

(51) Int. Cl.
| | | |
|---|---|---|
| C07H 21/04 | (2006.01) | |
| C12N 15/63 | (2006.01) | |
| C12N 15/85 | (2006.01) | |
| C12P 21/00 | (2006.01) | |

(52) U.S. Cl.
USPC ....... 536/24.1; 435/320.1; 435/325; 435/70.1

(58) Field of Classification Search
None
See application file for complete search history.

(56) References Cited

U.S. PATENT DOCUMENTS

| | | | |
|---|---|---|---|
| 4,215,051 A | 7/1980 | Schroeder et al. | |
| 4,897,355 A | 1/1990 | Eppstein et al. | |
| 4,946,787 A | 8/1990 | Eppstein et al. | |
| 5,049,386 A | 9/1991 | Eppstein et al. | |
| 6,524,792 B1 | 2/2003 | Renner | |
| 2002/0193330 A1 | 12/2002 | Hone et al. | |
| 2007/0048776 A1 | 3/2007 | Mauro et al. | |

FOREIGN PATENT DOCUMENTS

| | | |
|---|---|---|
| WO | 91/16024 | 10/1991 |
| WO | 91/17424 | 11/1991 |
| WO | 98/37189 | 8/1998 |
| WO | 99/24595 | 5/1999 |
| WO | WO-9925876 A1 | 5/1999 |
| WO | WO-9925896 A1 | 5/1999 |
| WO | 00/44896 | 8/2000 |
| WO | 01/55369 | 8/2001 |
| WO | 01/55371 | 8/2001 |
| WO | 01/71036 | 9/2001 |
| WO | 2007/025008 | 3/2007 |

OTHER PUBLICATIONS

Vivinus et al. (Eur. J. Biochem. vol. 268, pp. 1908-1917. 2001).*
Agren et al., *Immunol. Cell Biol.* 76:280, 1998.
Anderson, *Science* 256:808-813, 1992.
Benoist et al. *Nature* 290:304-310, 1981.
Bernstein et al., *Vaccine*, 17:1964, 1999.
Bollon et al., *J. Cin. Hematol. Oncol.* 10:39, 1980.
Boshart et al. *Cell* 41:521-530, 1985.
Botstein et al., *Miami Winter Symp.* 19:265, 1982.
Boyer et al., *J. Infect. Dis.*, 181:476, 2000.
Brisson et al., *Nature* 310:511-514, 1984.
Broach *Cell* 28:203, 1982.
Broglie et al., *Science* 224:838-843, 1984.
Capecchi, *TIG* 5:70, 1989.
Chappell et al. *Proc. Natl. Acad. Sci. USA* 101(26):9590-9594 (2004).
Chappell et al. *Proc. Natl. Acad. Sci. USA* 103(25):9488-9493 (2006).
Chappell et al. *Proc. Natl. Acad. Sci. USA* 97(4):1536-1541 (2000).
Cichutek, *Dev. Biol. Stand.*, 100:119, 1999.
Cone & Mulligan, *Proc. Natl. Acad. Sci. USA* 8 1:6349-6353, 1984.
Coruzzi et al., *EMBO J.* 3:1671-1680, 1984.
Davis et al., *J. Immunol.* 15:870, 1998.
Davis, *Microbes Infect.*, 1:7, 1999.
Dillon, *TIBTECH* 11:167-175, 1993.
Doetschman et al., *Nature* 330:576, 1987.
Donnelly et al., *Vaccine*, 15:865, 1997.
Eulalio et al. *Cell* 132:9-14 (2008).
Fuller et al., *Immunol. Cell Biol.*, 75: 389, 1997.
Fuller et al., *Vaccine*, 15:924, 1997.
Gowda et al., *J. Cell Biochem.*, 13D: 301, 1989.
Gurley et al., *Mol. Cell. Biol.*, 6:559-565, 1986.
Gurunathan et al., *Ann. Rev. Immunol.*, 18:927, 2000.
Hamer et al. *J. Mol. Appl. Gen.* 1:273, 1982.
Han et al. *Proc. Natl. Acad. Sci. USA*. 92:9747-9751, 1995.
Hayashi et al. *Vaccine*, 18: 3097-3105, 2000.
Hu et al. *Proc. Natl. Acad. Sci. USA* 96:1339-1344 (1999).
Huang et al., *Viral Immunol.*, 12:1, 1999.
Kodihalli et al., *J. Virol.*, 71: 3391, 1997.
Koncz et al., *EMBO J.* 2:1597-603, 1983.
Kozak *J. Cell Biol.* 108:229-241 (1989).
Kremer & Perricaudet, *Br. Med. Bull.* 51:31-44, 1995.
Krieg, *Biochim. Biophys. Acta.*, 1489:107, 1999.
Le et al., *Vaccine*, 18:1893, 2000.
Lee and Nathans, *J. Biol. Chem.* 263:3521, 1988.
Leitner, *Vaccine*, 18:765, 1999.
Lodmell et al. *Vaccine* 18:1059-1066, 2000.
Logan & Shenk, *Proc. Natl. Acad. Sci. USA* 81:3655-3659, 1984.
Mackett et al., *J. Virol.* 49:857-864, 1984.

(Continued)

Primary Examiner — Celine Qian
(74) Attorney, Agent, or Firm — Cooley LLP

(57) ABSTRACT

Provided are mRNA translational enhancer elements (TEEs), e.g., SEQ ID NOs:1-35. Also provided are translational enhancer polynucleotides that comprise one or more of the specific TEEs exemplified herein or their variants, homologs or functional derivatives. Further provided are expression vectors comprising such TEEs or translational enhancer polynucleotides, as well as host cells and expression systems that harbor such vectors.

14 Claims, 5 Drawing Sheets

(56) References Cited

OTHER PUBLICATIONS

Mackett et al., *Proc. Natl. Acad. Sci. USA*, 79:7415-7419, 1982.
Malone et al., *J. Biol. Chem.* 269:29903, 1994.
Mansour et al., *Nature* 336:348, 1988.
Mauro et al. *J. Biol. Chem* 283(48):33087-33093 (2008).
Meijer et al. *J. Biol. Chem* 275(40):30787-30793 (2000).
Miller, *Nature* 357:455-460, 1992.
Mitani & Caskey, *TIBTECH* 11:162-166, 1993.
Mulligan, *Science* 926-932, 1993.
Nabel & Feigner, *TIBTECH* 11:211-217, 1993.
Odell et al., *Nature*, 313:810, 1985.
Owens et al. *J. Biol. Chem* 98(4):1471-1476 (2001).
Panicali et al., *Proc. Natl. Acad. Sci. USA*, 79:4927-4931, 1982.
Peabody *J. Biol. Chem* 262(24):11847-11851 (1987).
Peabody *J. Biol. Chem* 264(9):5031-5035 (1989).
Sakaguchi et al., *Vaccine*, 14:747, 1996.
Sarver et al., *Mol. Cell. Biol.* 1:486, 1981.
Sasaki et al. *Inf. Immunol.* 65: 3520-3528, 1997.
Sasaki et al., *J. Virol.* 72:4931, 1998.
Schneerson et al. *J. Immunol.* 147:2136-2140, 1991.
Severin et al., *Plant Mol. Biol.*, 15:827, 1990.
Shaw et al., *Nucl. Acids Res.*, 12:7831-46, 1984.
Smith et al., *J. Biol.* 46:584, 1983.
Takamatsu et al., *EMBO J.*, 6:307-311, 1987.
Thomas et al., *Cell* 51:503, 1987.
Tsukamoto et al., *Virol.* 257:352, 1999.
Ulmer et al., *Vaccine* 18:18, 2000.
Van Brunt, *Biotechnology* 6:1149-1154, 1998.
Velten et al., *EMBO J.*, 3:2723, 1984.
Vigne et al., *Restorative Neurol. and Neurosci.* 8:35-36, 1995.
Webster et al, *Vacc.*, 12:1495-1498, 1994.
Weissbach & Weissbach, *Methods for Plant Molecular Biology*, Academic Press, NY, Section VIII, pp. 421-463, 1988.
Xin et al., *Clin. Immunol.*, 92:90, 1999.
Yao et al. *J. Virol.* 69:6249-6258, 1995.
Yu et al., *Gene Therapy* 1:13-26, 1994.
Zhou et al. *Proc. Natl. Acad. Sci. USA* 102(18):6273-6278 (2005).
Khan Asis et al: "Common inheritance of chromosome la associated with clonal expansion of Toxoplasma gondii.",Genome Research Sep. 2006 LNKD- PUBMED:16902086, vol. 16, No. 9, Sep. 2006, pp. 1119-1125, ISSN: 1088-9051 ; & DATABASE EMBL [Online] EBI, Hinxton, UK;May 9, 2006, Khan et al.: "Toxoplasma gondii RH, genomic DNA chromosome lb", Database accession No. AM055943.
Gray A et al: "Nucleotide sequence of epidermal growth factor cDNA predicts a 128,000-molecular weight protein precursor.", NATURE Jun. 23-29, 1983 LNKD- PUBMED:6304537, vol. 303, No. 5919, Jun. 23, 1983, pp. 722-725, ISSN: 0028-0836.
EMBL Database Accession No. ABQ67007.1, Jun. 1, 2007.
EMBL Database Accession No. CAN96185.1, retrieved Oct. 22, 2012.
EMBL Database Accession No. EB575177.1, Apr. 20, 2006.
EMBL Database Accession No. EM156564.1, Apr. 12, 2007.
EMBL Database Accession No. ES559169.1, May 24, 2007.
Database ENA [Online] Jan. 30, 2003, Wang et al.: "Sequence CB126433.1: K-EST0175509 L5HLK1s1 *Homo sapiens* cDNA clone L5HLK1s1-18-009;" XP002692711, retrieved from EBI Database accession No. CB126433.1 * abstract * & WANG Al-Guo et al: "Identification of intraheptic cholangiocarcinoma related genes by comparison with normal liver tissues using expressed sequence tags.", BioChemical and BioPhysical Research Communication Jul. 7, 2006, vol. 345, No. 3, Jul. 7, 2006, pp. 1022-1032, ISSN:0006-291X * the whole document *.
NCBI Database Accession No. NM003017, Nov. 17, 2006. Retrieved Jan. 29, 2013.
Chappell et al. "Ribosomal Tethering and Clustering as Mechanisms for Translation Initiaton." *PNAS.* 103.48(2006): 18077-18082.
ENA Accession No. BF2466781, Jan. 17, 2001.
ENA Accession No. BF846697.1, Jan. 17, 2001.
ENA Accession No. AC164957.2, Jul. 1, 2005.
Fussenegger et al. "Regulated Multicistronic Expression Technology for Mammalian Metabolic Engineering." *Cytotechnology.* 28.1-3(1998): 111-125.
Kräusslich et al. "Poliovirus Proteinase 2A Induces Cleavage of Eucaryotic Initiation Factor 4F Polypeptide p. 220." *J. Virol.* 61.9(1987): 2711-2718.
Vende et al. "Efficient Translation of Rotavirus mRNA Requires Simulataneous Interaction of NSP3 with the Eukaryotic Translation Initiation Factor eIF4G and the mRNA 3'End." *J. Virol.*74.15(2000): 7064-7071.
Zhou et al. "Isolation and Identification of Short Nucleotide Sequences that Affect Translation Initiation in *Saccharomyces cerevisiae.*" *PNAS.* 100.8(2003): 4457-4462.

* cited by examiner

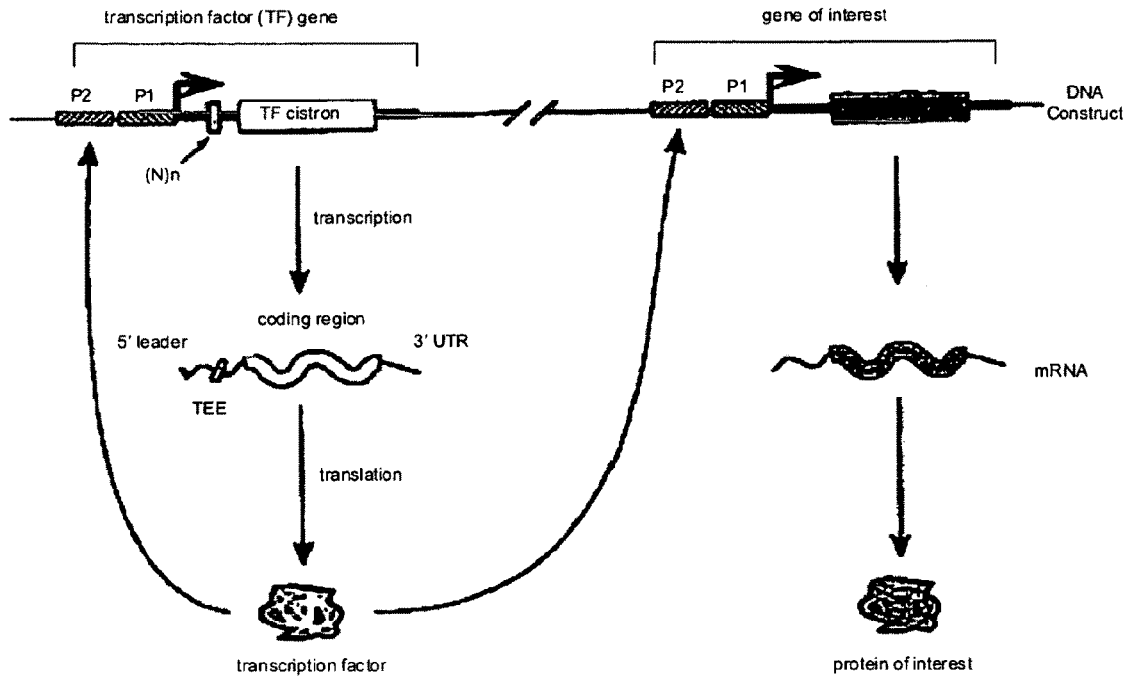

Promoter Elements:
- P1: - minimal promoter (TATA)
  - regulatable promoter
- P2: - upstream activating sequence (UAS; one to multiple copies)
  - T7 promoter
  - other transcription elements Transcription factor genes:
- GAL4, GAL4/VP16
- T7 RNA polymerase
- other transcription factors Genes of Interest:
- fluorescent protein genes (e.g. enhanced green fluorescent protein; EGFP)
- luciferase genes (*Renilla* or *Photinus*)
- therapeutic protein (e.g. monoclonal antibodies)

*FIG. 1*

SEQ ID NO:1
$\frac{A}{G}$ N $\frac{C}{G}$ G A G $\frac{A}{C}$ G $\frac{A}{G}$ $\frac{A}{C}$ $\frac{A}{G}$
R N S G A G M G R M R SEQ ID NO:2
$\frac{C}{A}$ $\frac{G}{C}$ C $\frac{G}{C}$ G C N G $\frac{A}{C}$ $\frac{A}{U}$ A
M S C S G C N G M W A

COMPOSITIONS AND METHODS RELATED TO MRNA TRANSLATIONAL ENHANCER ELEMENTS

REFERENCE TO PRIORITY DOCUMENT

This application claims the benefit of priority under 35 U.S.C. §119(e) of U.S. Provisional Patent Application Ser. No. 61/007,440, filed Dec. 11, 2007. Priority of the aforementioned filing date is hereby claimed and the disclosure of the provisional patent application is hereby incorporated by reference in its entirety.

BACKGROUND

Translation in eukaryotes is initiated following recruitment of the 40S ribosomal subunit, which can occur via the m7G cap-structure, a modified nucleotide found at the 5' ends of mRNAs, or through cap-independent mechanisms. The latter has been termed internal initiation of translation and can be mediated by various mechanisms. Following recruitment by either mechanism, the 40S ribosomal subunit moves to an initiation codon, the 60S ribosomal subunit joins, and peptide synthesis begins. Sequence elements contained within non-coding segments at the 5' and 3' ends of mRNAs can affect the efficiency of translation initiation. Sequence elements that can enhance the translation of a cap-dependent mRNA have been termed translational enhancer elements (TEEs).

Some TEEs enhance translation initiation by a mechanism that involves base pairing to the RNA component of 40S ribosomal subunits, the 18S ribosomal RNA (rRNA). Some TEEs can also function as ribosomal recruitment sites, facilitating internal initiation of translation; however, most internal ribosome entry sites (IRESes) do not function as TEEs.

SUMMARY

There is a need in the art for more TEEs which can be useful to regulate protein expression in biotechnology and gene therapy. The present disclosure addresses this and other needs.

In one aspect, provided are isolated or synthetic polynucleotide sequences which function as translation enhancers and include at least one mRNA translational enhancer element (TEE). The TEE present in the polynucleotide sequences consists of RNSGAGMGRMR (SEQ ID NO:1) or MSCSGCNGMWA (SEQ ID NO:2), or a substantially identical sequence thereof. Also, more than one copy (e.g., 2, 5, 10, 25, 50 or more copies) of each TEE can be present in these polynucleotide sequences.

In an embodiment, the TEE consists of $R_1N_1S_1GAGM_1GR_2M_2R_2R_3R_4$ (SEQ ID NO:3) or $R_5M_3S_2CS_3GCN_2GM_4WR_6$ (SEQ ID NO:4), or a substantially identical sequence thereof. In these sequences $R_1$ is absent, or A or G if present; $N_1$ is absent, or A, C or G if present, preferably A, C or G; $S_1$ is absent, or C or G if present, preferably C or G; $M_1$ is A or C; $R_2$ is absent, or A or G if present, preferably A or G, and $R_1$ and $R_2$ can be the same or different; $M_2$ is absent, or A or C if present, preferably A or C; $R_3$ is absent, or A or G if present, preferably absent; $R_4$ is absent, or C if present, preferably absent; and $R_5$ is absent, or A if present, preferably absent; $M_3$ is absent, or C or A if present, preferably C or A; $S_2$ is absent, or C or G if present, preferably C or G; $S_3$ is G or C; $N_2$ is G, C or T; $M_4$ is A or C; W is absent, or A or T if present and $R_6$ is absent, or A if present.

In another embodiment, the TEE consists of $R_1N_1S_1GAGM_1GR_2M_2R_2R_3R_4$. In this sequence $R_1$, $R_3$ and $R_4$ are absent; $N_1$ is A, C or G; $S_1$ is C or G; $M_1$ is A or C; $R_2$ is A or G and $M_2$ is A or C. In another embodiment, the TEE consists of $R_5M_3S_2CS_3GCN_2GM_4WR_6$. In this sequence $R_5$ and $R_6$ are absent; $M_3$ is absent, or A or C if present; $S_2$ is C or G; $S_3$ is C or G and $S_2$ and $S_3$ can be the same or different; $N_2$ is G, C or T; $M_2$ is A or C; W is absent, or A if present.

In some embodiments, the polynucleotide sequences include a TEE having a sequence that is at least 90% identical to a sequence from SEQ ID NOs: 5-35. In some embodiments, the polynucleotide sequences include a TEE having a sequence that is identical to one of the sequences of SEQ ID NOs: 5-35.

In some of the polynucleotide sequences, at least 2 copies of the TEE are present. In some of the polynucleotide sequences, more than 2 copies of the TEE are present. In some other embodiments, the polynucleotide sequences include at least 5 copies of the TEE, at least 10 copies, at least 25 or more copies of the TEE.

In a related aspect, provided are cloning or expression vectors for recombinantly expressing a polypeptide in a eukaryotic cell. The vectors contain a eukaryotic promoter which is operably-linked to a polynucleotide sequence that includes at least one mRNA translational enhancer element (TEE) disclosed herein. The TEE present in the vectors consists of RNSGAGMGRMR (SEQ ID NO: 1) or MSCSGCNGMWA (SEQ ID NO:2), or a substantially identical sequence thereof.

In an embodiment, the TEE present in the vectors consists of $R_1N_1S_1GAGM_1GR_2M_2R_2R_3R_4$ (SEQ ID NO:3) or $R_5M_3S_2CS_3GCN_2GM_4WR_6$ (SEQ ID NO:4), or a substantially identical sequence thereof. In these sequences $R_1$ is absent, or A or G if present; $N_1$ is absent, or A, C or G if present, preferably A, C or G; $S_1$ is absent, or C or G if present, preferably C or G; $M_1$ is A or C; $R_2$ is absent, or A or G if present, preferably A or G, and $R_1$ and $R_2$ can be the same or different; $M_2$ is absent, or A or C if present, preferably A or C; $R_3$ is absent, or A or G if present, preferably absent; $R_4$ is absent, or C if present, preferably absent; and $R_5$ is absent, or A if present, preferably absent; $M_3$ is absent, or C or A if present, preferably C or A; $S_2$ is absent, or C or G if present, preferably C or G; $S_3$ is G or C; $N_2$ is G, C or T; $M_4$ is A or C; W is absent, or A or T if present and $R_6$ is absent, or A if present.

In another embodiment, the TEE present in the vector consists of $R_1N_1S_1GAGM_1GR_2M_2R_2R_3R_4$. In this sequence $R_1$, $R_3$ and $R_4$ are absent; $N_1$ is A, C or G; $S_1$ is C or G; $M_1$ is A or C; $R_2$ is A or G and $M_2$ is A or C. In another embodiment, the TEE present in the vector consists of $R_5M_3S_2CS_3GCN_2GM_4WR_6$. In this sequence $R_5$ and & are absent; $M_3$ is absent, or A or C if present; $S_2$ is C or G; $S_3$ is C or G and $S_2$ and $S_3$ can be the same or different; $N_2$ is G, C or T; $M_2$ is A or C; W is absent, or A if present.

In some of the vectors, the TEEs consist of a sequence that is substantially identical to a sequence selected from SEQ ID NOs: 5-35. In some other vectors, the TEEs consist of a sequence that is identical to a sequence selected from SEQ ID NOs: 5-35.

In some vectors, the mRNA translational enhancer element is located 3' to the promoter and adapted for directional ligation of a second polynucleotide sequence encoding a polypeptide of interest. Some of these vectors further include a second polynucleotide sequence encoding a polypeptide of interest which is operably-linked to the mRNA translational enhancer element. In some vectors, the mRNA translational enhancer element is located in the 5' leader of the second polynucleotide sequence. Further provided are DNA vaccines which include a vector expressing an antigen of interest as disclosed herein. Further provided are host cells (e.g., eukaryotic host cells such as CHO cells) which are transfected with the vectors.

In a further aspect, provided are methods for recombinantly producing a polypeptide of interest. These methods entail constructing an expression vector which includes a eukaryotic promoter and at least one copy (e.g., 1, 2, 3, 4, 5, 10, 25, 50 or more copies) of a mRNA translational enhancer element that are each operably-linked to a polynucleotide encoding a polypeptide of interest. This is followed by transfecting the expression vector into a eukaryotic host cell (e.g., CHO cell), and then culturing the host cell transfected with the expression vector. In an embodiment, the mRNA translational enhancer element (TEE) present in the vectors consists of RNSGAGMGRMR (SEQ ID NO:1) or MSCSGCNGMWA (SEQ ID NO:2), or a substantially identical sequence thereof.

In an embodiment, the TEE present in the vectors consists of $R_1N_1S_1GAGM_1GR_2M_2R_2R_3R_4$ (SEQ ID NO:3) or $R_5M_3S_2CS_3GCN_2GM_4WR_6$ (SEQ ID NO:4), or a substantially identical sequence thereof. In these sequences $R_1$ is absent, or A or G if present; $N_1$ is absent, or A, C or G if present, preferably A, C or G; $S_1$ is absent, or C or G if present, preferably C or G; $M_1$ is A or C; $R_2$ is absent, or A or G if present, preferably A or G, and $R_1$ and $R_2$ can be the same or different; $M_2$ is absent, or A or C if present, preferably A or C; $R_3$ is absent, or A or G if present, preferably absent; $R_4$ is absent, or C if present, preferably absent; and $R_5$ is absent, or A if present, preferably absent; $M_3$ is absent, or C or A if present, preferably C or A; $S_2$ is absent, or C or G if present, preferably C or G; $S_3$ is G or C; $N_2$ is G, C or T; $M_4$ is A or C; W is absent, or A or T if present and $R_6$ is absent, or A if present.

In another embodiment, the TEE present in the vector consists of $R_1N_1S_1GAGM_1GR_2M_2R_2R_3R_4$. In this sequence $R_1$, $R_3$ and $R_4$ are absent; $N_1$ is A, C or G; $S_1$ is C or G; $M_1$ is A or C; $R_2$ is A or G and $M_2$ is A or C. In another embodiment, the TEE present in the vector consists of $R_5M_3S_2CS_3GCN_2GM_4WR_6$. In this sequence $R_5$ and $R_6$ are absent; $M_3$ is absent, or A or C if present; $S_2$ is C or G; $S_3$ is C or G and $S_2$ and $S_3$ can be the same or different; $N_2$ is G, C or T; $M_2$ is A or C; W is absent, or A if present.

The mRNA translational enhancer element can consist of a sequence that is substantially identical to a sequence selected from the group consisting of SEQ ID NOs: 5-35. In some methods, the mRNA translational enhancer element consists of a sequence that is identical to a sequence selected from the group consisting of SEQ ID NOs: 5-35. Some of the methods can further involve purifying the expressed recombinant polypeptide from the host cells or from the medium surrounding the cultured host cells. Various polypeptides of interest can be produced with the methods described herein. For example, a number of therapeutic proteins of great clinical importance are suitable for the methods.

A further understanding of the nature and advantages of the present invention may be realized by reference to the remaining portions of the specification and claims.

BRIEF DESCRIPTION OF THE DRAWINGS

FIG. 1 shows a schematic representation of a translation enhancer-driven positive feedback vector along with the various promoter (P1) and transcriptional enhancer (P2) sequences, transcription factor (TF) genes, and a protein of interest.

FIG. 4 shows consensus motifs deduced from various TEE elements.

DETAILED DESCRIPTION

I. Overview

Figure 2:
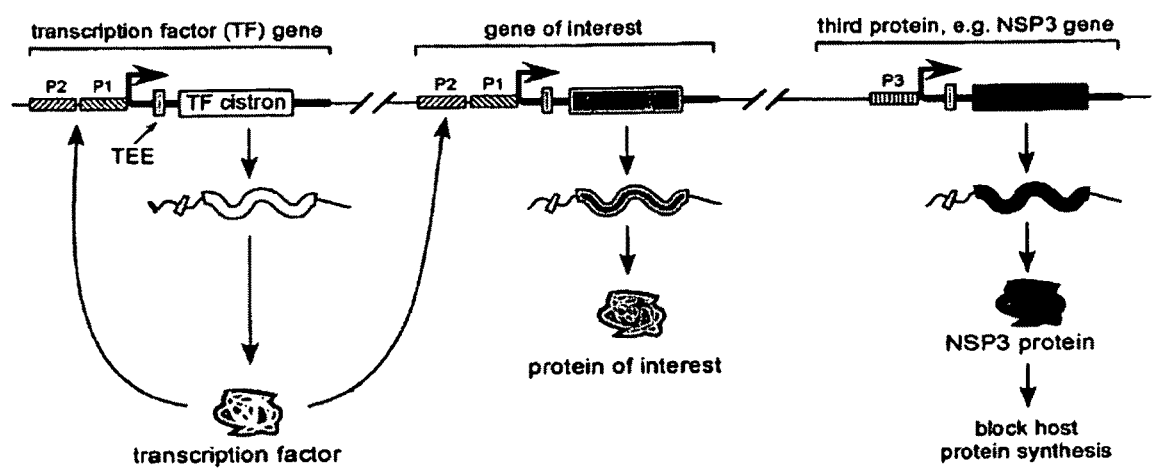
FIG. 2 shows a schematic representation of a translation enhancer-driven positive feedback vector as in FIG. 1 with a third protein to block host protein synthesis.

Disclosed herein are novel mRNA translational enhancer elements (TEEs). Specifically, and as detailed in the Examples below, identified are a number of short nucleotide sequences that are capable of enhancing translation in mammalian host cells (e.g., CHO and BHK cell lines). Disclosed are consensus motifs or TEEs from these short nucleotide sequences. In an embodiment, motif 1 is RNSGAGMGRMR (SEQ ID NO: 1), and motif 2 is MSCSGCNGMWA (SEQ ID NO:2). It is noted that in these sequences, R denotes A or G, M denotes A or C, S denotes G or C, W denotes A or U (T), and N denotes A, G, C or U (T).

In another embodiment, motif 1 is $R_1N_1S_1GAGM_1GR_2M_2R_2R_3R_4$ (SEQ ID NO: 3). In this sequence, $R_1$ is absent, or A or G if present; $N_1$ is absent, or A, C or G if present, preferably A, C or G; $S_1$ is absent, or C or G if present, preferably C or G; $M_1$ is A or C; $R_2$ is absent, or A or G if present, preferably A or G, and $R_1$ and $R_2$ can be the same or different; $M_2$ is absent, or A or C if present, preferably A or C; $R_3$ is absent, or A or G if present, preferably absent; $R_4$ is absent, or C if present, preferably absent. In another embodiment, motif 1 is $R_1N_1S_1GAGM_1GR_2M_2R_2R_3R_4$ (SEQ ID NO: 3) wherein $R_1$, $R_3$ and $R_4$ are absent; $N_1$ is A, C or G; $S_1$ is C or G; $M_1$ is A or C; $R_2$ is A or G and $M_2$ is A or C.

In another embodiment, motif 2 is $R_5M_3S_2CS_3GCN_2GM_4WR_6$ (SEQ ID NO:4). In this sequence, $R_5$ is absent, or A if present, preferably absent; $M_3$ is absent, or C or A if present, preferably C or A; $S_2$ is absent, or C or G if present, preferably C or G; $S_3$ is G or C; $N_2$ is G, C or T; $M_4$ is A or C; W is absent, or A or T if present and $R_6$ is absent, or A if present. In another embodiment, motif 2 is $R_5M_3S_2CS_3GCN_2GM_4WR_6$ (SEQ ID NO: 4) wherein $R_5$ and $R_6$ are absent; $M_3$ is absent, or A or C if present; $S_2$ is C or G; $S_3$ is C or G and $S_2$ and $S_3$ can be the same or different; $N_2$ is G, C or T; $M_2$ is A or C; W is absent, or A if present.

In addition, several specific sequences synthesized based on the consensus motifs are disclosed (e.g., SEQ ID NOS:5-35). These synthesized sequences are not represented in the sequences used to identify the motif sequences. The synthesized sequences exhibit enhanced translation activity. Polynucleotide sequences that contain one or multiple copies of these sequences are capable of enhancing translation by up to 25-fold.

Disclosed herein are translation enhancers which are isolated or substantially purified polynucleotides (e.g., DNA) which contain one or more copies of at least one mRNA translational enhancer element (TEE) disclosed herein. These polynucleotides can function as translation enhancers when operably-linked to a polynucleotide encoding a polypeptide of interest. Exemplary TEEs are shown in SEQ ID NOS:1-35. It is noted that while the TEEs are set forth herein in deoxyribonucleotide sequences one should readily appreciate TEEs or polynucleotides including the TEEs also encompass the corresponding ribonucleotide sequences. Also provided are cloning or expression vectors that contain the TEEs or translation enhancer polynucleotides disclosed herein, as well as host cells that harbor such vectors. Further provided are methods of employing the TEEs, the translation enhancer polynucleotides and the expression vectors to enhance translation and production of a desired polypeptide (e.g., a therapeutic protein).

The disclosed methods employ, unless otherwise indicated, conventional techniques of molecular biology (including recombinant techniques), microbiology, cell biology, biochemistry and immunology, which are within the skill of the art. Such techniques are explained fully in the literature. For example, exemplary methods are described in the following references, Sambrook et al., *Molecular Cloning: A Laboratory Manual*, Cold Spring Harbor Press ($3^{rd}$ ed., 2001); Brent et al., *Current Protocols in Molecular Biology*, John Wiley & Sons, Inc. (Ringbou ed., 2003); and Freshney, *Culture of Animal Cells: A Manual of Basic Technique*, Wiley-Liss, Inc. ($4^{th}$ ed., 2000).

II. Definitions

This specification is not limited to the particular methodology, protocols, and reagents described, as these may vary. It is also to be understood that the terminology used herein is for the purpose of describing particular embodiments only, and is not intended to limit the scope of the present invention which will be described by the appended claims.

As used herein, the singular forms "a", "ian", and "the" include plural reference unless the context clearly dictates otherwise. Thus, for example, reference to "a cell" includes a plurality of such cells, reference to "a protein" includes one or more proteins and equivalents thereof known to those skilled in the art, and so forth.

Unless defined otherwise, all technical and scientific terms used herein have the same meaning as commonly understood by those of ordinary skill in the art to which this disclosure pertains. The following references provide one of skill with a general definition of many of the terms used in this disclosure: *Academic Press Dictionary of Science and Technology*, Morris (Ed.), Academic Press ($1^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons ($3^{rd}$ ed., 2002); *Dictionary of Chemistry*, Hunt (Ed.), Routledge ($1^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press ($4^{th}$ ed., 2000). Further clarifications of some of these terms as they apply specifically to this disclosure are provided herein.

The term "agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "cistron" means a unit of DNA that encodes a single polypeptide or protein. The term "transcriptional unit" refers to the segment of DNA within which the synthesis of RNA occurs.

The term "DNA vaccines" refers to a DNA that can be introduced into a host cell or a tissue and therein expressed by cells to produce a messenger ribonucleic acid (mRNA) molecule, which is then translated to produce a vaccine antigen encoded by the DNA.

The language "gene of interest" is intended to include a cistron, an open reading frame (ORF), or a polynucleotide sequence which codes for a protein product (protein of interest) whose production is to be regulated by the translational enhancer elements (TEEs). Examples of genes of interest include genes encoding therapeutic proteins, nutritional proteins and industrial useful proteins. Genes of interest can also include reporter genes or selectable marker genes such as enhanced green fluorescent protein (EGFP), luciferase genes (*Renilla* or *Photinus*).

Expression is the process by which a polypeptide is produced from DNA. The process involves the transcription of the gene into mRNA and the subsequent translation of the mRNA into a polypeptide.

The term "endogenous" as used herein refers to a gene normally found in the wild-type host, while the term "exogenous" refers to a gene not normally found in the wild-type host.

A "host cell" refers to a living cell into which a heterologous polynucleotide sequence is to be or has been introduced. The living cell includes both a cultured cell and a cell within a living organism. Means for introducing the heterologous polynucleotide sequence into the cell are well known, e.g., transfection, electroporation, calcium phosphate precipitation, microinjection, transformation, viral infection, and/or the like. Often, the heterologous polynucleotide sequence to be introduced into the cell is a replicable expression vector or cloning vector. In some embodiments, host cells can be engineered to incorporate a desired gene on its chromosome or in its genome. Many host cells can be employed (e.g., CHO cells) and serve as hosts as is well known in the art. See, e.g., Sambrook et al., *Molecular Cloning. A Laboratory Manual*, Cold Spring Harbor Press ($3^{rd}$ ed., 2001); and Brent et al., *Current Protocols in Molecular Biology*, John Wiley & Sons, Inc. (ringbou ed., 2003). In some embodiments, the host cell is a eukaryotic cell.

The term "homolog" refers to a sequence which has a structure (e.g., nucleotide sequence) that is substantially identical to that of a reference sequence (e.g., the specific mRNA translational enhancer elements disclosed herein). Typically, the homolog maintains the ability to enhance translation of an mRNA encoded by a gene of interest. Homologs may be screened for activity by creating mutations in the reference sequence described above, inserting the mutated sequence at an appropriate position in an expression vector containing a promoter operably linked to a reporter gene or a gene of interest. The expression vector can then be introduced into a host cell to examine translation of the protein encoded by the gene. If translation from the reporter gene is the same as that of the reporter gene under the control of the reference enhancer sequence then the mutated sequence is a functional homolog.

The term "inducing agent" is used to refer to a chemical, biological or physical agent that effects translation from an inducible translational regulatory element. In response to exposure to an inducing agent, translation from the element generally is initiated de novo or is increased above a basal or constitutive level of expression. An inducing agent can be, for example, a stress condition to which a cell is exposed, for example, a heat or cold shock, a toxic agent such as a heavy metal ion, or a lack of a nutrient, hormone, growth factor, or the like; or can be a compound that affects the growth or differentiation state of a cell such as a hormone or a growth factor.

The phrase "isolated or purified polynucleotide" is intended to include a piece of polynucleotide sequence (e.g., DNA) which has been isolated at both ends from the sequences with which it is immediately contiguous in the naturally occurring genome of the organism. The purified polynucleotide can be an oligonucleotide which is either double or single stranded; a polynucleotide fragment incorporated into a vector; a fragment inserted into the genome of a eukaryotic or prokaryotic organism; or a fragments used as a probe. The phrase "substantially pure," when referring to a polynucleotide, means that the molecule has been separated from other accompanying biological components so that, typically, it has at least 85 percent of a sample or greater percentage.

The term "nucleotide sequence," "nucleic acid sequence," "nucleic acid," or "polynucleotide sequence," refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. Nucleic acid sequences can be, e.g., prokaryotic sequences, eukaryotic mRNA sequences, cDNA sequences from eukaryotic mRNA, genomic DNA sequences from eukaryotic DNA (e.g., mammalian DNA), and synthetic DNA or RNA sequences, but are not limited thereto.

The term "promoter" means a nucleic acid sequence capable of directing transcription and at which transcription is initiated. A variety of promoter sequences are known in the art. For example, such elements can include, but are not limited to, TATA-boxes, CCAAT-boxes, bacteriophage RNA polymerase specific promoters (e.g., T7, SP6, and T3 promoters), an SP1 site, and a cyclic AMP response element. If the promoter is of the inducible type, then its activity increases in response to an inducing agent.

The five prime leader or untranslated region (5' leader, 5' leader sequence or 5' UTR) is a particular section of messenger RNA (mRNA) and the DNA that codes for it. It starts at the +1 position (where transcription begins) and ends just before the start codon (usually AUG) of the coding region. In bacteria, it may contain a ribosome binding site (RBS) known as the Shine-Delgamo sequence. The 5' leader may be a hundred or more nucleotides long, and the 3' UTR may be even longer (up to several kilobases in length).

The term "operably linked" or "operably associated" refers to functional linkage between genetic elements that are joined in a manner that enables them to carry out their normal functions. For example, a gene is operably linked to a promoter when its transcription is under the control of the promoter and the transcript produced is correctly translated into the protein normally encoded by the gene. Similarly, a translational enhancer element is operably associated with a gene of interest if it allows up-regulated translation of a mRNA transcribed from the gene.

A sequence of nucleotides adapted for directional ligation, e.g., a polylinker, is a region of an expression vector that provides a site or means for directional ligation of a polynucleotide sequence into the vector. Typically, a directional polylinker is a sequence of nucleotides that defines two or more restriction endonuclease recognition sequences, or restriction sites. Upon restriction cleavage, the two sites yield cohesive termini to which a polynucleotide sequence can be ligated to the expression vector. In an embodiment, the two restriction sites provide, upon restriction cleavage, cohesive termini that are non-complementary and thereby permit directional insertion of a polynucleotide sequence into the cassette. For example, the sequence of nucleotides adapted for directional ligation can contain a sequence of nucleotides that defines multiple directional cloning means. Where the sequence of nucleotides adapted for directional ligation defines numerous restriction sites, it is referred to as a multiple cloning site.

The term "subject" for purposes of treatment refers to any animal classified as a mammal, e.g., human and non-human mammals. Examples of non-human animals include dogs, cats, cattle, horses, sheep, pigs, goats, rabbits, and etc. Except when noted, the terms "patient" or "subject" are used herein interchangeably. In an embodiment, the subject is human.

Transcription factor refers to any polypeptide that is required to initiate or regulate transcription. For example, such factors include, but are not limited to, c-Myc, c-Fos, c-Jun, CREB, cEts, GATA, GAL4, GAL4/Vp16, c-Myb, MyoD, NF-κB, bacteriophage-specific RNA polymerases, Hif-1, and TRE. Example of sequences encoding such factors include, but are not limited to, GenBank accession numbers K02276 (c-Myc), K00650 (c-fos), BC002981 (c-jun), M27691 (CREB), X14798 (cEts), M77810 (GATA), K01486 (GAL4), AY136632 (GAL4/Vp16), M95584 (c-Myb), M84918 (MyoD), 2006293A (NF-κB), NP 853568 (SP6 RNA polymerase), AAB28111 (T7 RNA polymerase), NP 523301 (T3 RNA polymerase), AF364604 (HIF-1), and X63547 (TRE).

A "substantially identical" nucleic acid or amino acid sequence refers to a nucleic acid or amino acid sequence which includes a sequence that has at least 90% sequence identity to a reference sequence as measured by one of the well known programs described herein (e.g., BLAST) using standard parameters. The sequence identity can be at least 95%, at least 98%, and at least 99%. In some embodiments, the subject sequence is of about the same length as compared to the reference sequence, i.e., consisting of about the same number of contiguous amino acid residues (for polypeptide sequences) or nucleotide residues (for polynucleotide sequences).

Sequence identity can be readily determined with various methods known in the art. For example, the BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)). Percentage of sequence identity is determined by comparing two optimally-aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "translational enhancer element (TEE)" refers to cis-acting sequences that increase the amount of polypeptide or protein produced from an mRNA, above the translation level from the cap-structure alone. Examples of TEEs known in the art include sequences in the 5'-leader of the Gtx homeodomain protein (Chappell et al., Proc. Natl. Acad. Sci. USA 101:9590-9594, 2004). In addition, novel TEEs are disclosed herein, e.g., SEQ ID NOs:1-35. Unless otherwise noted, TEEs refer to both the translation enhancing elements in mRNA sequences and the corresponding coding sequence elements in DNA sequences.

"Translational enhancer polynucleotides" or "translation enhancer polynucleotide sequences" are polynucleotides which include one or more of the specific TEE exemplified herein (i.e., SEQ ID. NOs:1-35) or their variants, homologs or functional derivatives. One or multiple copies of a specific TEE can be present in the polynucleotides. The TEEs in the translational enhancer polynucleotides can be organized in one or more sequence segments. A sequence segment can harbor one or more of the specific TEEs exemplified herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the specific TEEs exemplified herein, identical or different number of copies of each of the specific TEEs, and/or identical or different organization of the TEEs within each sequence segment.

The term "treating" or "alleviating" includes the administration of compounds or agents to a subject to prevent or delay the onset of the symptoms, complications, or biochemical indicia of a disease (e.g., a cardiac dysfunction), alleviating the symptoms or arresting or inhibiting further development of the disease, condition, or disorder. Subjects in need of treatment include patients already suffering from the disease or disorder as well as those prone to have the disorder or those in whom the disorder is to be prevented.

Treatment may be prophylactic (to prevent or delay the onset of the disease, or to prevent the manifestation of clinical or subclinical symptoms thereof) or therapeutic suppression or alleviation of symptoms after the manifestation of the disease. In the treatment of cardiac remodeling and/or heart failure, a therapeutic agent may directly decrease the pathology of the disease, or render the disease more susceptible to treatment by other therapeutic agents.

The term "vector" or "construct" refers to polynucleotide sequence elements arranged in a definite pattern of organization such that the expression of genes/gene products that are operably linked to these elements can be predictably controlled. Typically, they are transmissible polynucleotide sequences (e.g., plasmid or virus) into which a segment of foreign DNA can be spliced in order to introduce the foreign DNA into host cells to promote its replication and/or transcription.

A cloning vector is a DNA sequence (typically a plasmid or phage) which is able to replicate autonomously in a host cell, and which is characterized by one or a small number of restriction endonuclease recognition sites. A foreign DNA fragment may be spliced into the vector at these sites in order to bring about the replication and cloning of the fragment. The vector may contain one or more markers suitable for use in the identification of transformed cells. For example, markers may provide tetracycline or ampicillin resistance.

An expression vector is similar to a cloning vector but is capable of inducing the expression of the DNA that has been cloned into it, after transformation into a host. The cloned DNA is usually placed under the control of (i.e., operably linked to) certain regulatory sequences such as promoters or enhancers. Promoter sequences may be constitutive, inducible or repressible.

III. Translational Enhancer Polynucleotides and Recombinant Vectors

Provided herein are isolated or substantially purified polynucleotides which function as translational enhancers. These translational enhancer polynucleotides include the specific mRNA translational enhancer elements (TEEs) disclosed herein or their variants, homologs or functional derivatives. The translational enhancer polynucleotides can contain one or more sequence segments including the consensus Motif 1 (SEQ ID NO: 1), Motif 2 (SEQ ID NO:2), Motif 1a (SEQ ID NO: 3), or Motif 2a (SEQ ID NO: 4). Some of the translational enhancer polynucleotides can contain one or more sequence segments that include one of the specific mRNA TEEs shown in SEQ ID NOs:5-35. As demonstrated in the Examples below, expression of a polypeptide of interest in a vector that harbors one of these mRNA TEEs results in significant increase of protein production. In addition to the mRNA TEEs shown in SEQ ID NOs:1-35, the mRNA TEEs also can encompass sequences that are substantially identical to one of these exemplified sequences and can retain the basic functional characteristic of enhancing the expression of an operably linked gene of interest in a host cell.

A sequence segment in the translational enhancer polynucleotides can contain just one specific mRNA TEE or several of the mRNA TEEs shown in SEQ ID NOs:1-35. For each of the specific mRNA TEEs present in a sequence segment, there can be just one copy of the mRNA TEE in the sequence segment. Alternatively, multiple copies of each of the mRNA TEEs can be present in each sequence segment. Typically, the different mRNA TEE elements in the translational enhancer polynucleotides can be operatively linked adjacent to each other or separated by spacer nucleotide sequences that can vary from 1 to about 100 nucleotides in length. Some translational enhancer polynucleotides contain only one sequence segment. Some other translational enhancer polynucleotides contain a plurality of sequence segments. In the latter embodiments, the sequence segments can be homogenous or heterogeneous.

Thus, some embodiments relate to a translational enhancer polynucleotide sequence segment which includes a mRNA TEE sequence that is the same or substantially identical to one of the sequences shown in SEQ ID NOs:1-35. Some other embodiments relate to a translational enhancer polypeptide sequence segment which contains 2, 3, 4, 5, 10, 25, 50 or more copies of a specific mRNA TEE shown in SEQ ID NOs:1-35. In some embodiments, the translational enhancer polynucleotides relate to a sequence segment which contains more than one (e.g., 2, 3, 4, 5, or more) of the different mRNA TEEs shown in SEQ ID NOs:1-35 or their variants or homologs. In these embodiments, each of the specific mRNA TEEs can be present in one or more copies (e.g., 2, 3, 4, 5, 10, 25 or more copies). In still some other embodiments, the translational enhancer polynucleotides contain more than one of the sequence segments noted above. The different sequence segments can be identical in terms of the types of specific mRNA TEEs and the number of copies of each specific mRNA TEE harbored therein. Alternatively, the multiple sequence segments can be different in the types of specific mRNA TEEs and/or the number of copies of each of the specific mRNA TEEs. In any of these embodiments, other than the mRNA TEEs shown in SEQ ID NOs:1-35, variants of these specific TEEs or homologs with substantially sequence identity can also be used.

The specific mRNA TEEs or translational enhancer polynucleotides disclosed herein can be used to construct recombinant cloning vectors or expression vectors. Such vectors are useful for expressing a polypeptide or protein of interest, e.g., a therapeutic protein. They can also be employed in therapeutic applications such as DNA vaccines or gene therapy. The recombinant vectors can be constructed from a plasmid, virus or other vehicles known in the art by insertion or incorporation of one or more of the specific mRNA TEEs or translational enhancer polynucleotides described herein. Examples of such vehicles are discussed in the Examples below. Typically, the vectors contain a promoter suitable for expression a polypeptide of interest in a host cell (e.g., mammalian host cells). In the vectors, a TEE-containing sequence is operably linked to the promoter, e.g., at 3' to the promoter. The TEE-containing sequence can be one of the specific TEEs shown in SEQ ID NOs:1-35, a sequence segment including a TEE or a translational enhancer polynucleotide as described above. The vectors can additionally harbor a sequence of nucleotides adapted for directional ligation of a polynucleotide sequence encoding a polypeptide of interest. For example, a polylinker can be employed for cloning the polynucleotide sequence so that the cloned sequence is operably linked to and put under the control of the promoter and the TEE-containing sequence. Polylinkers are polynucleotide sequences that can have a series of three or more closely spaced restriction endonuclease recognition sequences (see, e.g., Sambrook et al., supra). In some embodiments, as illustrated in the Examples, the vectors allow the polynucleotide sequence to be cloned into the vectors at a position so that the TEE is present in the 5' leader of the transcribed mRNA encoding the polypeptide of interest.

In addition to the promoter and the TEE-containing sequence, some recombinant vectors described herein further contain a gene of interest or a polynucleotide encoding a protein or a polypeptide of interest. The gene of interest or the polynucleotide sequence is operably linked to a promoter sequence and the TEE which facilitate the efficient transcription of the inserted polynucleotide sequence in a host cell. Translation of eukaryotic mRNA initiates at AUG codon which encodes methionine of an mRNA. For this reason, the linkage between a promoter and the gene of interest should not contain any intervening codons for methionine. The presence of such codons may result in the formation of a fusion protein (if the AUG codon is in the same reading frame as the gene of interest) or the formation of a peptide that either terminates upstream of the authentic initiation codon or overlaps the gene, but in a different reading frame. In some embodiments, the gene of interest which encodes a protein includes the 5' leader and 3' untranslated (UTR) sequences. In some other embodiments, the 5' leader and/or 3' untranslated regions in the output transcription product are already present in the vector prior to cloning of the gene of interest. In these embodiments, at least one TEE is located in the 5' leader and/or the 3' untranslated regions.

Typically, the translational enhancer is located between the transcription promoter and the AUG codon. The exact position of the TEEs relative to the promoter and the cap site of the gene of interest is not critical; however, the exact position may affect efficiency. For instance, some TEEs can enhance translation when located in the 5' leader of the encoded mRNA, or in the 3' untranslated region. In some embodiments, the TEE is situated in the 5' leader sequence of the gene of interest or a cistron. In these embodiments, the enhancer element is positioned within about 1-500 nucleotides, particularly within about 1-100 or about 1-50 nucleotides of the translation start site.

By incorporating a translational enhancer polynucleotide described above, the recombinant vectors can have one or more of the specific translational enhancer elements shown in SEQ ID NOs:1-35. For any of these specific enhancer elements, the vectors can harbor just one copy of the enhancer element or multiple copies of the same enhancer element. For example, to increase polypeptide expression from an associated cistron, concatemers of 2, 5, 10, 20, 35, 50 or 75 copies of a specific TEE shown in SEQ ID NOs:1-35 can be present in some of the recombinant expression vectors. Some other vectors have multiple sequence segments which independently can include one or more of the specific TEE sequences exemplified herein.

In addition, the recombinant or expression vectors can contain additional sequence elements. For example, the vector can contain an origin of replication, as well as specific markers which allow phenotypic selection of the transfected or transformed host cells. Other elements present in the vectors will vary depending upon host cell type, but will generally include sequences involved in the initiation of transcription and translation and sequences signaling the termination of transcription. Transcriptional enhancer sequences may also be present. The vectors can also include coding sequences within the same transcription unit, controlling elements such as ribosome binding sites, and polyadenylation sites, additional transcription units under control of the same or a different promoter, sequences that permit cloning, expression, and transformation of a host cell. In some embodiments, the vectors include a polynucleotide that encodes a signal peptide that directs the polypeptide encoded by the cloned gene of interest to the surface of the host cell. In some embodiments, the vectors can also include a polynucleotide that encodes a molecular tag that can facilitate separation of a host cell that expresses the reporter gene from a host cell that does not express the reporter gene.

In some embodiments, the recombinant vectors are intended for expressing a protein of interest in eukaryotic host cells. As detailed below, these include various mammalian cells as well as insect cells or plant cells. In some embodiments, provided are DNA vaccines which expresses a target antigen from an expression vector disclosed herein. A large number of vectors suitable for use in eukaryotes are known in the art. Examples include the pMSXND expression vector for expression in mammalian cells (Lee and Nathans, J. Biol. Chem. 263:3521, 1988); baculovirus-derived vectors for expression in insect cells; and other vectors for eukaryotic expression as described in Botstein et al., Miami Winter Symp. 19:265, 1982; Broach Cell 28:203, 1982; Bollon et al., J. Cin. Hematol. Oncol. 10:39, 1980; and *Cell Biology. A Comprehensive Treatise*, Goldstein and Prescott (eds.), Academic Press Inc., U.S. (1980). In some embodiments, the translational enhancer elements or polynucleotides are incorporated into DNA constructs designed for homologous recombination. Such constructs are described, e.g., in Capecchi, TIG 5:70, 1989; Mansour et al., Nature 336:348, 1988; Thomas et al., Cell 51:503, 1987; and Doetschman et al., Nature 330:576, 1987.

For vectors expressing a protein of interest, the mRNA TEEs or translational enhancer polynucleotides are typically present in the vectors operably linked to regulatory elements such as a promoter, as noted above. Depending on the specific protein of interest and vector/host system to be used, many different promoters can be employed in the recombinant vectors. Examples of promoters that can be used include the promoter of the mouse metallothionein I gene (Hamer et al. J. Mol. Appl. Gen. 1:273, 1982); the immediate early and TK promoters of Herpes virus (Yao et al. J. Virol. 69:6249-6258, 1995); the SV 40 early promoter (Benoist et al. Nature 290: 304-310, 1981); and the human CMV promoter (Boshart et al. Cell 41:521-530, 1985); the 35S RNA and 19S RNA promoters of CaMV (Brisson et al., Nature, 310:511, 1984; Odell et al., Nature, 313:810, 1985); the full-length transcript promoter from Figwort Mosaic Virus (FMV) (Gowda et al., J. Cell Biochem., 13D: 301, 1989) and the coat protein promoter from TMV (Takamatsu et al., EMBO J. 6:307, 1987). Additional promoters that can be used to construct recombinant expression vectors include the light-inducible promoter from the small subunit of ribulose bis-phosphate carboxylase (ssRUBISCO) (Coruzzi et al., EMBO J., 3:1671, 1984; and Broglie et al., Science, 224:838, 1984); mannopine synthase promoter (Velten et al., EMBO J., 3:2723, 1984); nopaline synthase (NOS) promoter (Shaw et al., Nucl. Acids Res., 12:7831-46, 1984); octopine synthase (OCS) promoter (Koncz et al., EMBO J. 2:1597-603, 1983); and heat shock promoters, e.g., soybean hsp17.5-E or hsp17.3-B (Gurley et al., Mol. Cell. Biol., 6:559, 1986; Severin et al., Plant Mol. Biol., 15:827, 1990).

Promoters can include both constitutive and inducible natural promoters as well as engineered promoters. The CaMV promoters are examples of constitutive promoters. To be most useful, an inducible promoter should 1) provide low expression in the absence of the inducer; 2) provide high expression in the presence of the inducer; 3) employ an induction scheme that does not interfere with the normal physiology of the plant; and 4) have no effect on the expression of other genes.

In some embodiments, the recombinant vectors can optionally contain a selectable marker. The marker typically encodes a trait or a phenotype which permits the selection of, or the screening for, a host cell containing the marker. In an embodiment, the marker gene is an antibiotic resistance gene whereby the appropriate antibiotic can be used to select for transformed plant cells from among cells that are not transformed. Examples of suitable selectable markers include adenosine deaminase, dihydrofolate reductase, hygromycin-B-phosphotransferase, thymidine kinase, xanthine-guanine phospho-ribosyltransferase and amino-glycoside 3'-O-phosphotransferase II (kanamycin, neomycin and G418 resistance). Other suitable markers will be known to those of skill in the art, e.g., screenable markers such as the GUS reporter gene (uidA), luciferase or the GFP gene.

IV. Host Cells for Enhanced Production of Polypeptides of Interest

The translational enhancer polynucleotides and related vectors are useful in various industrial and therapeutic applications. In some embodiments, provided are methods of using such expression vector/host cell systems for expressing therapeutic proteins or proteins with industrial utility at increased levels. For example, therapeutic proteins that can be expressed with the vectors can include therapeutic antibodies such as HerceptinS, polypeptide antigens from various pathogens such as disease causing bacteria or viruses (e.g., E. coli, P. aeruginosa, S. aureus, malaria, HIV, rabies virus, HBV, and cytomegalovirus), and other proteins such as lactoferrin, thioredoxin and beta-caseinvaccines. Other suitable proteins or polypeptides suitable include, e.g., nutritionally important proteins; growth promoting factors; proteins for early flowering in plants; proteins giving protection to the plant under certain environmental conditions, e.g., proteins conferring resistance to metals or other toxic substances, such as herbicides or pesticides; stress related proteins which confer tolerance to temperature extremes; proteins conferring resistance to fungi, bacteria, viruses, insects and nematodes; proteins of specific commercial value, e.g., enzymes involved in metabolic pathways, such as EPSP synthase.

The recombinant vectors harboring the gene of interest and the mRNA TEEs or enhancer polynucleotides described herein can be introduced into an appropriate host cell by any means known in the art. For example, the vector can be transfected into the host cell by calcium phosphate co-precipitation, by conventional mechanical procedures such as microinjection or electroporation, by insertion of a plasmid encased in liposomes, and by virus vectors. These techniques are all well known and routinely practiced in the art, e.g., Brent et al., *Current Protocols in Molecular Biology*, John Wiley & Sons, Inc. (ringbou ed., 2003); and Weissbach & Weissbach, *Methods for Plant Molecular Biology*, Academic Press, NY, Section VIII, pp. 42 1-463, 1988. Host. cells which harbor the transfected recombinant vector can be identified and isolated using the selection marker present on the vector. Large numbers of recipient cells may then be grown in a medium which selects for vector-containing cells. These cells may be used directly or the expressed recombinant protein may be purified in accordance with conventional methods such as extraction, precipitation, chromatography, affinity methods, electrophoresis and the like. The exact procedure used will depend upon the specific protein produced and the specific vector/host expression system utilized.

In an embodiment, host cells for expressing the recombinant vectors are eukaryotic cells. Eukaryotic vector/host systems, and mammalian expression systems, allow for proper post-translational modifications of expressed mammalian proteins to occur, e.g., proper processing of the primary transcript, glycosylation, phosphorylation and advantageously secretion of expressed product. Therefore, eukaryotic cells such as mammalian cells can be the host cells for the protein of a polypeptide of interest. Examples of such host cell lines include CHO, BHK, HEK293, VERO, HeLa, COS, MDCK, NS0 and W138.

In some embodiments, engineered mammalian cell systems that utilize recombinant viruses or viral elements to direct expression of the protein of interest are employed. For example, when using adenovirus expression vectors, the coding sequence of a protein of interest along with a TEE or translational enhancer polynucleotide may be ligated to an adenovirus transcription/translation control complex, e.g., the late promoter and tripartite leader sequence. This chimeric gene may then be inserted into the adenovirus genome by in vitro or in vivo recombination. Insertion in a non-essential region of the viral genome (e.g., region E1 or E3) will result in a recombinant virus that is viable and capable of expressing the polypeptide of interest in infected hosts (e.g., see Logan & Shenk, Proc. Natl. Acad. Sci. USA 81:3655-3659, 1984). Alternatively, the vaccinia virus 7.5K promoter may be used. (e.g., see, Mackett et al., *Proc. Natl. Acad. Sci. USA*, 79:7415-7419, 1982; Mackett et al., *J. Virol.* 49:857-864, 1984; Panicali et al., *Proc. Natl. Acad. Sci. USA*, 79:4927-4931, 1982). Of particular interest are vectors based on bovine papilloma virus which have the ability to replicate as extrachromasomal elements (Sarver et al., *Mol. Cell. Biol.* 1:486, 1981). These vectors can be used for stable expression by including a selectable marker in the plasmid, such as the neo gene. Alternatively, the retroviral genome can be modified for use as a vector capable of introducing and directing the expression of the gene of interest in host cells (Cone & Mulligan, Proc. Natl. Acad. Sci. USA 8 1:6349-6353, 1984).

High level expression may also be achieved using inducible promoters, including, but not limited to, the metallothionine IIA promoter and heat shock promoters.

The host cell for expression of the recombinant vectors can also be yeast. In yeast, a number of vectors containing constitutive or inducible promoters may be used. See, e.g., Brent et al., *Current Protocols in Molecular Biology*, John Wiley & Sons, Inc. (ringbou ed., 2003); and *The Molecular Biology of the Yeast Saccharomyces*, Strathem et al. (eds.), Cold Spring Harbor Press (1982). A constitutive yeast promoter such as ADH or LEU2 or an inducible promoter such as GAL may be used. Alternatively, vectors may be used which promote integration of foreign DNA sequences into the yeast chromosome.

In cases where plant expression vectors are used, the expression of a gene of interest may be driven by any of a number of promoters. For example, viral promoters such as the $^{35}$S RNA and 19S RNA promoters of CaMV (Brisson et al., Nature 310~511-514, 1984) or the coat protein promoter to TMV (Takamatsu et al., EMBO J., 6:307-3 11, 1987) may be used. Alternatively, plant promoters such as the small subunit of RUBISCO (Coruzzi et al., EMBO J. 3:1671 1680, 1984; and Broglie et al., Science 224:838-843, 1984) or heat shock promoters (Gurley et al., Mol. Cell. Biol., 6:559-565, 1986) may be used.

An alternative expression system that can be used to express a protein of interest with the recombinant vectors is an insect system. In one such system, *Autographa californica* nuclear polyhedrosis virus (AcNPV) is used as a vector to express foreign genes. The virus grows in *Spodoptera frugiperda* cells. The zinc finger-nucleotide binding polypeptide coding sequence may be cloned into non-essential regions of the virus and placed under control of an AcNPV promoter (e.g., the polyhedrin promoter). Successful insertion of the zinc finger-nucleotide binding polypeptide coding sequence will result in inactivation of the polyhedrin gene and production of non-occluded recombinant virus (i.e., virus lacking the proteinaceous coat coded for by the polyhedrin gene). These recombinant viruses are then used to infect cells in which the inserted gene is expressed. See, e.g., Smith et al., J. Biol. 46:584, 1983; and Smith, U.S. Pat. No. 4,215,051).

Once the recombinant vector has been introduced into the appropriate host cells, the expressed recombinant protein may be purified in accordance with conventional methods such as extraction, precipitation, chromatography, affinity chromatography, electrophoresis and the like. The exact procedure used will depend upon both the specific protein produced and the specific expression system utilized. For long-term, high-yield production of recombinant proteins, stable expression is preferred. Rather than using expression vectors which contain origins of replication, host cells can be transformed with a vector that allows stable integration of the vector into the host chromosomes. Host cells with stably integrated polynucleotides that encode the protein of interest can grow to form foci which in turn can be cloned and expanded into cell lines. For example, following the introduction of foreign DNA, engineered cells may be allowed to grow for 1-2 days in an enriched media, and then switched to a selective media.

V. Therapeutic Applications

Further provided are vector systems that can be employed in various therapeutic applications. For example, a vector for therapeutic expression of proteins can be constructed with an mRNA TEE or translational enhancer polynucleotide described above and a polynucleotide encoding a therapeutic protein. Other examples include vectors to be used in vaccines so that increased antigen production can be achieved.

In some embodiments, the translational enhancer elements and polynucleotides disclosed herein are used in the preparation of DNA vaccines. In order to produce increased antigen levels, the DNA vaccines can be generally comprised of an expression vector wherein expression of a vaccine antigen is enhanced by the presence of one or more of the translational enhancer elements (e.g., SEQ ID NOs: 1-35). In some embodiments, the DNA vaccines can deliver and express more than one antigen. Other than sequences encoding the vaccine antigen and the translational enhancer elements, the DNA vaccine vector typically also includes a promoter for transcription initiation that is active in eukaryotic cells. Such DNA vaccine vectors can be generated in accordance with the methods well known in the art. For example, methods for making and using DNA vaccine for a given antigen are described in, e.g., Gurunathan et al., Ann. Rev. Immunol., 18:927, 2000; Krieg, Biochim. Biophys. Acta., 1489:107, 1999; Cichutek, Dev. Biol. Stand., 100:119, 1999; Davis, Microbes Infect., 1:7, 1999; and Leitner, Vaccine, 18:765, 1999.

Any of the vectors described above may be employed to express a vaccine antigen in the DNA vaccines. Additional vectors that can be used to construct DNA vaccines can include viral vectors such as ALVAC (a canarypox virus), MVA (a cowpox variant), and ADV5 (adenovirus 5) vectors, as well as plasmid vectors such as pUC19 (ATCC#37254), pcDNA3.1 (Invitrogen, Carlsbad, Calif.), pNGVL (National Gene Vector Laboratory, University of Michigan, Mich.), p414cyc (ATCC#87380), pBSL130 (ATCC#87145), and pECV25 (ATCC#77187). Examples of promoters that can be employed in the vaccine vectors include, e.g., the SV40 early promoter, the cytomegalovirus immediate early promoter/enhancer, and various eukaryotic promoters described herein.

A diverse array of vaccine antigens can be expressed by the DNA vaccines. These include, e.g., HIV-1 antigens, Hepatitis C virus antigens, Hepatitis B virus antigens, Herpes Simplex viral antigens, Pox virus antigens, Influenza virus antigens, Measles virus antigens, Dengue virus antigens, *Entamoeba histolytica* antigens, Semliki Forest virus antigens, Papilloma virus antigens, *Plasmodium vivax* and *Plasmodium falciparum* antigens. Additional information of antigens that can be expressed in the DNA vaccines can be obtained from the website of DNAvaccine.com.

The DNA vaccines can be used to immunize any subject in need of prevention or protection against infection of a pathogen (e.g., HIV infection). Such subjects include humans and non-human animals such as rodents (e.g. mice, rats and guinea pigs), swine, chickens, ferrets, non-human primates. Methods of administering a DNA vaccine to a suitable subject are described in the art. See, e.g., Webster et al, Vacc., 12:1495-1498, 1994; Bernstein et al., Vaccine, 17:1964, 1999; Huang et al., Viral Immunol., 12:1, 1999; Tsukamoto et al., Virol. 257:352, 1999; Sakaguchi et al., Vaccine, 14:747, 1996; Kodihalli et al., J. Virol., 71: 3391, 1997; Donnelly et al., Vaccine, 15:865, 1997; Fuller et al., Vaccine, 15:924, 1997; Fuller et al., Immunol. Cell Biol., 75: 389, 1997; Le et al., Vaccine, 18:1893, 2000; Boyer et al., J. Infect. Dis., 181: 476, 2000.

In addition to enhancing expression of the vaccine antigens by using one or more of the specific TEEs or mRNA translational enhancer polynucleotides described herein, the DNA vaccines can also be formulated with an adjuvant. Suitable adjuvants that can be employed include, e.g., aluminum phosphate or aluminum hydroxyphosphate, monophosphoryl-lipid A, QS-21 saponin, dexamethasone, CpG DNA sequences, Cholera toxin, cytokines or chemokines. Such adjuvants enhance immunogenicity of the DNA vaccines. Methods of preparing such modified DNA vaccines are known in the art. See, e.g., Ulmer et al., Vaccine 18:18, 2000; Schneerson et al. J. Immunol. 147:2136-2140, 1991; Sasaki et al. Inf. Immunol. 65: 3520-3528, 1997; Lodmell et al. Vaccine 18:1059-1066, 2000; Sasali et al., J. Virol. 72:4931, 1998; Malone et al., J. Biol. Chem. 269:29903, 1994; Davis et al., J. Immunol. 15:870, 1998; Xin et al., Clin. Immunol., 92:90, 1999; Agren et al., Immunol. Cell Biol. 76:280, 1998; and Hayashi et al. Vaccine, 18: 3097-3105, 2000.

In some embodiments, provided are methods for enhancing expression of a therapeutic protein in the treatment of various diseases. In these methods, an expression vector harboring a translational enhancer element or polynucleotide and expressing a therapeutic protein are transfected into target cells, ex vivo or in vivo, through the interaction of the vector and the target cell. The compositions are administered to a subject in an amount sufficient to elicit a therapeutic response in the subject. Such gene therapy procedures have been used to correct acquired and inherited genetic defects, cancer, and viral infection in a number of contexts. See, e.g., Anderson, Science 256:808-813, 1992; Nabel & Felgner, TIBTECH 11:211-217, 1993; Mitani & Caskey, TIBTECH 11:162-166, 1993; Mulligan, Science 926-932, 1993; Dillon, TIBTECH 11: 167-175, 1993; Miller, Nature 357:455-460, 1992; Van Brunt, Biotechnology 6:1149-1154, 1998; Vigne et al., Restorative Neurol. and Neurosci. 8:35-36, 1995; Kremer & Perricaudet, Br. Med. Bull. 51:31-44, 1995; Haddada et al., in *Current Topics in Microbiology and Immunology* (Doerfler & Bohm eds., 1995); and Yu et al., Gene Therapy 1: 13-26, 1994.

Various diseases and disorders are suitable for treatment with the therapeutic methods described herein. These include malignancies of the various organ systems, e.g., lung, breast, lymphoid, gastrointestinal, and genito-urinary tract. Also suitable for treatment are adenocarcinomas which include malignancies such as most colon cancers, renal-cell carcinoma, prostate cancer, non-small cell carcinoma of the lung, cancer of the small intestine, and cancer of the esophagus. A recombinant expression vector containing an mRNA TEE or translational enhancer polynucleotide disclosed herein is also useful in treating non-malignant cell-proliferative diseases such as psoriasis, pemphigus vulgaris, Behcet's syndrome, and lipid histiocytosis. Essentially, any disorder that can be treated or ameliorated with a therapeutic protein is considered susceptible to treatment with an expression vector that expresses the therapeutic protein at increased level due to the presence of the translational enhancer element in the vector.

A large number of delivery methods can be used to practice the therapeutic methods described herein. These methods are all well known to those of skill in the art. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. No. 5,049,386, U.S. Pat. No. 4,946,787; and U.S. Pat. No. 4,897,355 and lipofection reagents are sold commercially (e.g., Transfectam™ and Lipofectin™). Cationic and neutral lipids that are suitable for efficient receptor-recognition lipofection of polynucleotides include those described in, e.g., WO 91/17424 and WO 91/16024. Delivery can be to cells (ex vivo administration) or target tissues (in vivo administration).

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al. (Proc. Natl. Acad. Sci. USA. 92:9747-9751, 1995) reported that Moloney murine leukemia virus can be modified to express human hereguiin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

The expression vectors can be delivered in vivo by administration to an individual subject, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual subject (e.g., lymphocytes, bone marrow aspirates, tissue biopsy) or universal donor hematopoietic stem cells, followed by reimplantation of the cells into a subject, usually after selection for cells which have incorporated the vector. Ex vivo cell transfection for diagnostics, research, or for gene therapy (e.g., via re-infusion of the transfected cells into the host organism) is well known to those of skill in the art. In an embodiment, cells can be isolated from the subject organism, transfected with a nucleic acid (gene or cDNA), and re-infused back into the subject organism (e.g., subject). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from subjects).

EXAMPLES

The following examples are provided as further illustration, but not to limit the scope. Other variants will be readily apparent to one of ordinary skill in the art and are encompassed by the appended claims.

Example 1

Positive Feedback Vector System for Identifying Translational Enhancers

Identification of TEEs involved use of a dual-monocistronic positive feedback vector: one cistron encoding Gal4VP16 transcription factor, the other encoding *Renilla* luciferase. Both cistrons contain a minimal promoter with 4-copies of the Upstream Activating Sequence (UAS), which enhances transcription when bound to Gal4VP16. When introduced into cells, the minimal promoters drive very low levels of both mRNAs and encoded proteins. Introduction of a sequence that can enhance translation into the 5' leader of the Gal4VP16 cistron drives translation of the Gal4VP16 mRNA. The Gal4VP16 protein can then bind to both promoters, increasing transcription, driving its own transcription and that of the other cistron via specific binding sites in the promoters of the two genes thereby initiating a positive feedback loop. TEEs were identified from libraries of random nucleotide sequences. In an embodiment, only cistrons encoding enhanced GFP (EGFP) were used and improved the signal-to-noise ratios allowing for isolation of a single library plasmid per transfected cell. Confirmation involved testing in both the positive feedback system and an unamplified vector system.

FIG. 1 illustrates a schematic representation of the positive feedback vector along with the various promoter (P1) and transcriptional enhancer (P2) sequences, transcription factor (TF) genes, and a gene of interest. The transcription factor gene and the gene of interest may be on the same plasmid or on different plasmids. For the selection application, a random nucleotide sequence (N), n nucleotides in length, is present in the 5' leader of the transcription factor mRNA. A sequence that functions as a translational enhancer element (TEE) will facilitate the translation of this mRNA. The encoded transcription factor will then bind to sites in the promoters of the two genes and increase their transcription. In one embodiment, the construct expresses two mRNAs: one encoding a protein of interest which may be a reporter protein and the other encoding a transcription factor. The transcription of both mRNAs is driven by minimal promoters but can be enhanced by the expression of the transcription factor via binding sites for the transcription factor that are located in the promoters of both genes. A small amount of transcription factor mRNA is expressed from the minimal promoter but the translation of this mRNA is blocked by an obstacle in the 5' leader of the mRNA encoding the transcription factor. This obstacle may be a stable stem-loop structure and/or upstream AUG initiation codons. The synthesis of this transcription factor is dependent on the presence of a translation enhancer in the mRNA encoding this factor.

FIG. 2 illustrates a translation enhancer-driven positive feedback vector with a third protein to block host protein synthesis. The first two genes (transcription factor gene and gene of interest) are the same as in FIG. 1 except that all three mRNAs contain a TEE in their 5' leader. The third protein (e.g., the Rotavirus NSP3 protein) will increase the translation of the first two encoded mRNAs by blocking the translation of host mRNAs and reducing the competition from them. The third gene is under the transcriptional control of promoter P3, which is either a constitutive promoter or an inducible promoter. P3 may also include promoter elements P1 and P2. For the selection application, the mRNAs for the gene of interest and third protein will contain a known TEE, while the transcription factor gene will contain a random nucleotide sequence. In this scenario, the TEE is resistant to the activity of the third protein. For a protein production application, all three genes may contain a known TEE that is resistant to the activity of the third protein. The three genes may be on one, two, or three different plasmids.

More detailed procedures of employing the positive feedback system to identify TEEs are previously described in, e.g., PCT publication WO2007/025008.

Example 2

Identification of Consensus Translational Enhancer Motifs

Figure 3:
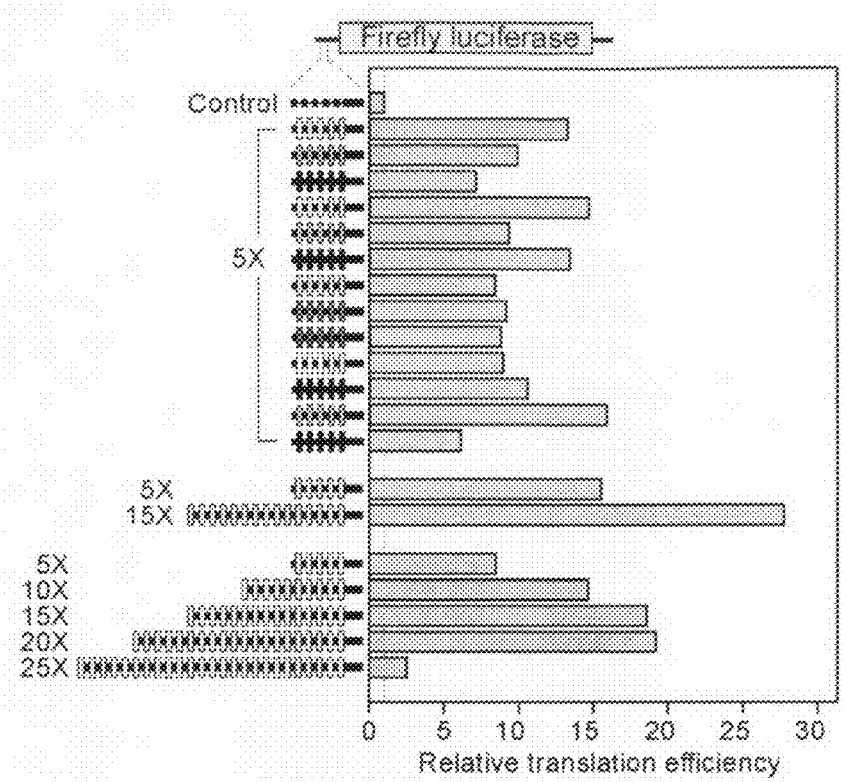
FIG. 3 shows translation enhancing activities of translational enhancement by 5 to 25 copies (5×-25×) of various TEE elements in CHO cells relative to the activity of a size-matched control construct. In the first group of 13 bars below the Control, SEQ ID NO: 31 (4'3) is represented by bar 6. The last group of 5 bars represents SEQ ID NO: 31 (4'3).

Using a dual monocistronic positive feedback vector system as described above, numerous short nucleotide sequences that function as translational enhancers in Chinese Hamster Ovary (CHO) and other cell lines, including BHK (Baby hamster Kidney) cells were identified. These translational enhancer elements (TEEs) range in length from seven to twelve nucleotides. As shown in FIG. 3, multiple copies of these TEEs increased protein production by up to 25-fold in CHO cells. In each example, there are at least 5 linked copies of the same TEE in the 5' leader of the Firefly luciferase cistron. The first construct is a size-matched control which contains no TEEs. Constructs were transiently transfected into CHO cells and assayed after 2 days. Translation efficiencies are relative to the activity of the size-matched control construct. In FIG. 3, the top 13 bars under the control bar correspond respectively to results obtained with 5 copies of 13 different TEEs. The next two bars show translation enhancing activities of another TEE at 5 or 15 copies. The bottom bars illustrate the translation enhancing activities of yet another TEE sequence when 5-25 copies were employed.

Several of these TEEs showed sequence similarities, and putative consensus motifs were identified from these TEEs (see FIG. 4). Sequences of two embodiments of the TEE motifs are as follows: RNSGAGMGRMR (SEQ ID NO: 1), and MSCSGCNGMWA (SEQ ID NO:2). It is noted that in these sequences, R denoted A or G, M denotes A or C, S denotes G or C, W denotes A or U, and N denotes A, G, C or U.

In another embodiment, Motif 1a sequence is $R_1N_1S_1GAGM_1GR_2M_2R_2R_3R_4$ (SEQ ID NO: 3). In this sequence, $R_1$ is absent, or A or G if present; $N_1$ is absent, or A, C or G if present, preferably A, C or G; $S_1$ is absent, or C or G if present, preferably C or G; $M_1$ is A or C; $R_2$ is absent, or A or G if present, preferably A or G, and $R_1$ and $R_2$ can be the same or different; $M_2$ is absent, or A or C if present, preferably A or C; $R_3$ is absent, or A or G if present, preferably absent; $R_4$ is absent, or C if present, preferably absent. In another embodiment, the Motif 1a sequence is $R_1N_1S_1GAGM_1GR_2M_2R_2R_3R_4$ (SEQ ID NO: 3), wherein $R_1$, $R_3$ and $R_4$ are absent; $N_1$ is A, C or G; $S_1$ is C or G; $M_1$ is A or C; $R_2$ is A or G and $M_2$ is A or C.

In another embodiment, the Motif 2a sequence is $R_5M_3S_2CS_3GCN_2GM_4WR_6$ (SEQ ID NO:4). In this sequence, $R_5$ is absent, or A if present, preferably absent; $M_3$ is absent, or C or A if present, preferably C or A; $S_2$ is absent, or C or G if present, preferably C or G; $S_3$ is G or C; $N_2$ is G, C or T; $M_4$ is A or C; W is absent, or A or T if present and $R_6$ is absent, or A if present. In another embodiment, the Motif 2a sequence is $R_5M_3S_2CS_3GCN_2GM_4WR_6$ (SEQ ID NO: 4), wherein $R_5$ and $R_6$ are absent; $M_3$ is absent, or A or C if present; $S_2$ is C or G; $S_3$ is C or G and $S_2$ and $S_3$ can be the same or different; $N_2$ is G, C or T; $M_2$ is A or C; W is absent, or A if present.

Example 3

Activities of Synthetic mRNA Translational Enhancer Elements

Figure 5:
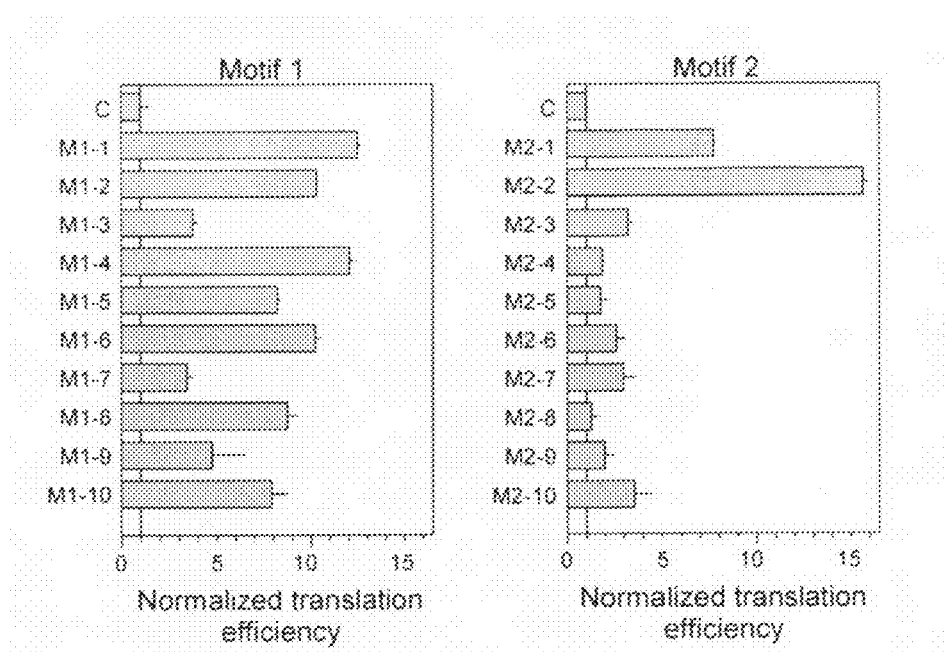
FIG. 5 shows translation enhancing activities of synthetic sequences based on motif sequence I (SEQ ID NO: 1) or motif sequence 2 (SEQ ID NO:2) relative to the activity of a size-matched control construct.

Based on the consensus motifs noted above, various specific TEE sequences corresponding to generally to Motifs 1 and 2 were synthesized and tested for translation enhancing activity (see SEQ ID NOs: 5-35 of Table 1). DNA fragments containing the test sequences were generated from two overlapping, complementary oligonucleotides that were synthesized and annealed to each other. The annealed oligonucleotides had unbasepaired nucleotides at each end, providing sticky ends for cloning into the vector using EcoR1 and BamH1. The fragments were cloned into the 5' leader of a luciferase reporter mRNA in the positive feedback expression vector as described in Example 1. The *Renilla* luciferase constructs containing the motif sequences were then transiently transfected into CHO cells. Cells were assayed after 3 days for the ability of the test sequences to enhance translation. A size matched control (reference) plasmid contained polyA in the cloning region. Effects of the TEEs on translation efficiency of the reporter polypeptide are shown in FIG. 5.

The results indicate that the consensus motifs are predictive of translation enhancing activity of a TEE which corresponds to one of these motifs. Also as indicated in the figure, TEE sequences based on Motif 1 tend to enhance translation to higher levels than those based on Motif 2.

TABLE 1

Sequences of synthetic TEEs corresponding to consensus motifs 1 (M1) and 2 (M2)

| TEE | Nucleotide sequence | SEQ ID NO |
|---|---|---|
| M1-1 | GCGAGAGAA | 5 |
| M1-2 | GGGAGCGAA | 6 |
| M1-3 | GCGAGAGGA | 7 |
| M1-4 | GCGAGCGGA | 8 |
| M1-5 | CGGAGCGAA | 9 |
| M1-6 | CGGAGCGGA | 10 |
| M1-7 | ACGAGAGGA | 11 |
| M1-8 | ACGAGCGGA | 12 |
| M1-9 | GACGAGAGGA | 13 |
| M1-10 | GACGAGAGAA | 14 |
| M1-11 | AGCGAGCG | 15 |
| M1-12 | AGGAGAGGA | 16 |
| M1-13 | GCCGAGAGA | 17 |
| M1-14 | CGAGAGGCA | 18 |
| M1-15 | GAGAGGAGC | 19 |
| M2-1 | CGCGGCGGA | 20 |
| M2-2 | CGCCGCCGC | 21 |
| M2-3 | GCGGCTGAA | 22 |
| M2-4 | CCGGCTGAA | 23 |
| M2-5 | CGCCGCTGAA | 24 |
| M2-6 | CGCCGCGGAA | 25 |
| M2-7 | CGCCGCCGAA | 26 |
| M2-8 | CCCGCGGAA | 27 |

TABLE 1-continued

Sequences of synthetic TEEs corresponding to consensus motifs 1 (M1) and 2 (M2)

| TEE | Nucleotide sequence | SEQ ID NO |
|---|---|---|
| M2-9 | CCCGCCGAA | 28 |
| M2-10 | CCCGCTGAA | 29 |
| M2-11 | CCCGGCGGA | 30 |
| M2-12 | CGCGGCTGA | 31 |
| M2-13 | CGGCTGCTA | 32 |
| M2-14 | CCCGGCGGA | 33 |
| M2-15 | AGCCGCCGCA | 34 |
| M2-16 | ACGCCGCCGA | 35 |

The novel translational enhancers described herein can have various practical and industrial applications. For example, they can minimize the costs associated with industrial scale cultures and reduce drug costs. Higher protein concentrations can also facilitate protein purification. In addition, these enhancers may enable processes that may otherwise not be possible due to poor protein expression, e.g. expressing enough antigen from a DNA vaccine to generate an immune response. These translational enhancers can be used to dramatically increase the yield of specific proteins in mammalian cells. For example, many therapeutic proteins are expressed in CHO cells, which are the most commonly used cells for the large scale production of therapeutic proteins, to ensure proper post-transcriptional processing. In addition to industrial protein production, translational enhancers have potential use in various vector systems. For example, for research purposes, therapeutic expression of proteins, and DNA vaccines, for increasing antigen production.

While this specification contains many specifics and described with references to preferred embodiments thereof, these should not be construed as limitations on the scope of an invention that is claimed or of what may be claimed, but rather as descriptions of features specific to particular embodiments. It will be understood by those skilled in the art that various changes in form and details may be made therein without departing from the meaning of the invention described. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. The scope of the invention is defined by the claims that follow.

All publications, databases, GenBank sequences, patents, and patent applications cited in this specification are herein incorporated by reference as if each was specifically and individually indicated to be incorporated by reference.

What is claimed is:

1. An isolated polynucleotide sequence comprising at least two mRNA translational enhancer elements (TEE), wherein at least one TEE consists of a full-length sequence that is selected from the group consisting of 5'-CGCGGCTGA-3' (SEQ ID NO: 31), 5'-AGCCGCCGCA-3' (SEQ ID NO: 34) and 5'-ACGCCGCCGA-3' (SEQ ID NO: 35).

2. The polynucleotide sequence of claim 1 which comprises at least 5 copies of the TEE.

3. The polynucleotide sequence of claim 1 which comprises at least 10 copies of the TEE.

4. A vector for recombinantly expressing a polypeptide in a eukaryotic cell, comprising a eukaryotic promoter operably linked to a polynucleotide sequence comprising at least one mRNA translational enhancer element (TEE), wherein the TEE is selected from the group consisting of 5'-CGCG-GCTGA-3' (SEQ ID NO: 31), 5'-AGCCGCCGCA-3' (SEQ ID NO: 34) and 5'-ACGCCGCCGA-3' (SEQ ID NO: 35).

5. The vector of claim 4, wherein the mRNA translational enhancer element is located 3 to the promoter and adapted for directional ligation of a second polynucleotide sequence encoding a polypeptide of interest.

6. The vector of claim 4, further comprising a second polynucleotide sequence encoding a polypeptide of interest which is operably linked to the mRNA translational enhancer element.

7. The vector of claim 6, wherein the mRNA translational enhancer element is located in the 5' leader sequence of the second polynucleotide sequence.

8. A DNA vaccine comprising the vector of claim 4.

9. An isolated eukaryotic host cell transfected with the vector of claim 4.

10. The host cell of claim 9, wherein the host cell is a CHO cell.

11. A method for recombinantly producing a polypeptide comprising:
   (i) constructing an expression vector which comprises a eukaryotic promoter and a mRNA translational enhancer element that are each operably linked to a polynucleotide encoding the polypeptide, wherein the TEE is selected from the group consisting of 5'-CGCG-GCTGA-3' (SEQ ID NO: 31), 5'-AGCCGCCGCA-3' (SEQ ID NO: 34) and 5'-ACGCCGCCGA-3' (SEQ ID NO: 35);
   (ii) transfecting the expression vector into a eukaryotic host cell; and
   (iii) culturing the host cell transfected with the expression vector; thereby producing the polypeptide.

12. The method of claim 11, further comprising purifying the recombinant polypeptide.

13. The method of claim 11, wherein the host cell is CHO cell.

14. The method of claim 11, wherein the polypeptide is a therapeutic protein.

* * * * *

SEQUENCE LISTING

<160> NUMBER OF SEQ ID NOS: 35

<210> SEQ ID NO 1
<211> LENGTH: 11
<212> TYPE: DNA
<213> ORGANISM: Artificial Sequence
<220> FEATURE:
<223> OTHER INFORMATION: Synthesized Translation Enhancer Element
      Putative Consensus Motif 2
<220> FEATURE:
<221> NAME/KEY: misc_feature
<222> LOCATION: (1)..(1)
<223> OTHER INFORMATION: M denotes A or C
<220> FEATURE:
<221> NAME/KEY: misc_feature
<222> LOCATION: (2)..(2)
<223> OTHER INFORMATION: S denotes G or C
<220> FEATURE:
<221> NAME/KEY: misc_feature
<222> LOCATION: (4)..(4)
<223> OTHER INFORMATION: S denotes G or C
<220> FEATURE:
<221> NAME/KEY: misc_feature
<222> LOCATION: (7)..(7)
<223> OTHER INFORMATION: N denotes A, G, C or U(T)
<220> FEATURE:
<221> NAME/KEY: misc_feature
<222> LOCATION: (9)..(9)
<223> OTHER INFORMATION: M denotes A or C
<220> FEATURE:
<221> NAME/KEY: misc_feature
<222> LOCATION: (10)..(10)
<223> OTHER INFORMATION: W denotes A or U(T)

<400> SEQUENCE: 1
mscsgcngmw a                                                             11

<210> SEQ ID NO 2
<211> LENGTH: 11
<212> TYPE: DNA
<213> ORGANISM: Artificial Sequence
<220> FEATURE:
<223> OTHER INFORMATION: Synthesized Translation Enhancer Element
      Putative Consensus Motif 1
<220> FEATURE:
<221> NAME/KEY: misc_feature
<222> LOCATION: (1)..(1)
<223> OTHER INFORMATION: R denotes A or G
<220> FEATURE:
<221> NAME/KEY: misc_feature
<222> LOCATION: (2)..(2)
<223> OTHER INFORMATION: N denotes A, G, C or U(T)
<220> FEATURE:
<221> NAME/KEY: misc_feature
<222> LOCATION: (3)..(3)
<223> OTHER INFORMATION: S denotes G or C
<220> FEATURE:
<221> NAME/KEY: misc_feature
<222> LOCATION: (7)..(7)
<223> OTHER INFORMATION: M denotes A or C
<220> FEATURE:
<221> NAME/KEY: misc_feature
<222> LOCATION: (9)..(9)
<223> OTHER INFORMATION: R denotes A or G
<220> FEATURE:
<221> NAME/KEY: misc_feature
<222> LOCATION: (10)..(10)
<223> OTHER INFORMATION: M denotes A or C
<220> FEATURE:
<221> NAME/KEY: misc_feature
<222> LOCATION: (11)..(11)
<223> OTHER INFORMATION: R denotes A or G

<400> SEQUENCE: 2
rnsgagmgrm r                                                             11

```
<210> SEQ ID NO 3
<211> LENGTH: 13
<212> TYPE: DNA
<213> ORGANISM: Artificial sequence
<220> FEATURE:
<223> OTHER INFORMATION: Synthesized Translation Enhancer Element
      Putative Consensus Motif 1a
<220> FEATURE:
<221> NAME/KEY: misc_feature
<222> LOCATION: (1)..(1)
<223> OTHER INFORMATION: R1 is absent, or A or G if present;
<220> FEATURE:
<221> NAME/KEY: misc_feature
<222> LOCATION: (2)..(2)
<223> OTHER INFORMATION: N1 is absent, or A,C or G if present,
      preferably A, C or G;
<220> FEATURE:
<221> NAME/KEY: misc_feature
<222> LOCATION: (3)..(3)
<223> OTHER INFORMATION: S1 is absent, or C or G if present, preferably
      C or G;
<220> FEATURE:
<221> NAME/KEY: misc_feature
<222> LOCATION: (7)..(7)
<223> OTHER INFORMATION: M1 is A or C;
<220> FEATURE:
<221> NAME/KEY: misc_feature
<222> LOCATION: (9)..(9)
<223> OTHER INFORMATION: R2 is absent, or A or G if present, preferably
      A or G, and R1 and R2 can be the same or different;
<220> FEATURE:
<221> NAME/KEY: misc_feature
<222> LOCATION: (10)..(10)
<223> OTHER INFORMATION: M2 is absent, or A or C if present, preferably
      A or C;
<220> FEATURE:
<221> NAME/KEY: misc_feature
<222> LOCATION: (11)..(11)
<223> OTHER INFORMATION: R2 is absent, or A or G if present, preferably
      A or G, and R1 and R2 can be the same or different;
<220> FEATURE:
<221> NAME/KEY: misc_feature
<222> LOCATION: (12)..(12)
<223> OTHER INFORMATION: R3 is absent, or A or G if present, preferably
      absent;
<220> FEATURE:
<221> NAME/KEY: misc_feature
<222> LOCATION: (13)..(13)
<223> OTHER INFORMATION: R4 is absent, or C if present, preferably
      absent.

<400> SEQUENCE: 3
rnsgagmgrm rrr                                                      13

<210> SEQ ID NO 4
<211> LENGTH: 12
<212> TYPE: DNA
<213> ORGANISM: Artificial sequence
<220> FEATURE:
<223> OTHER INFORMATION: Synthesized Translation Enhancer Element
      Putative Consensus Motif 2a
<220> FEATURE:
<221> NAME/KEY: misc_feature
<222> LOCATION: (1)..(1)
<223> OTHER INFORMATION: R5 is absent, or A if present, preferably
      absent;
<220> FEATURE:
<221> NAME/KEY: misc_feature
<222> LOCATION: (2)..(2)
<223> OTHER INFORMATION: M3 is absent, or C or A if present, preferably
      C or A;
<220> FEATURE:
<221> NAME/KEY: misc_feature
<222> LOCATION: (3)..(3)
<223> OTHER INFORMATION: S2 is absent, or C or G if present, preferably
```

```
             C or G;
<220> FEATURE:
<221> NAME/KEY: misc_feature
<222> LOCATION: (5)..(5)
<223> OTHER INFORMATION: S3 is G or C;
<220> FEATURE:
<221> NAME/KEY: misc_feature
<222> LOCATION: (8)..(8)
<223> OTHER INFORMATION: N2 is G, C or T;
<220> FEATURE:
<221> NAME/KEY: misc_feature
<222> LOCATION: (10)..(10)
<223> OTHER INFORMATION: M4 is A or C;
<220> FEATURE:
<221> NAME/KEY: misc_feature
<222> LOCATION: (11)..(11)
<223> OTHER INFORMATION: W is absent, or A or T if present
<220> FEATURE:
<221> NAME/KEY: misc_feature
<222> LOCATION: (12)..(12)
<223> OTHER INFORMATION: R6 is absent, or A if present.

<400> SEQUENCE: 4
rmscsgcngm wr                                                         12

<210> SEQ ID NO 5
<211> LENGTH: 9
<212> TYPE: DNA
<213> ORGANISM: Artificial Sequence
<220> FEATURE:
<223> OTHER INFORMATION: Synthesized Translation Enhancer Element
      Oligonucleotide M1-1 corresponding generally to TEE Consensus
      Motif 1

<400> SEQUENCE: 5 gcgagagaa                                                              9

<210> SEQ ID NO 6
<211> LENGTH: 9
<212> TYPE: DNA
<213> ORGANISM: Artificial Sequence
<220> FEATURE:
<223> OTHER INFORMATION: Synthesized Translation Enhancer Element
      Oligonucleotide M1-2 corresponding generally to TEE Consensus
      Motif 1

<400> SEQUENCE: 6 gggagcgaa                                                              9

<210> SEQ ID NO 7
<211> LENGTH: 9
<212> TYPE: DNA
<213> ORGANISM: Artificial Sequence
<220> FEATURE:
<223> OTHER INFORMATION: Synthesized Translation Enhancer Element
      Oligonucleotide M1-3 corresponding generally to TEE Consensus
      Motif 1

<400> SEQUENCE: 7 gcgagagga                                                              9

<210> SEQ ID NO 8
<211> LENGTH: 9
<212> TYPE: DNA
<213> ORGANISM: Artificial sequence
<220> FEATURE:
<223> OTHER INFORMATION: Synthesized Translation Enhancer Element
      Oligonucleotide M1-4 corresponding generally to TEE Consensus
      Motif 1

<400> SEQUENCE: 8
``` gcgagcgga                                                                9

<210> SEQ ID NO 9
<211> LENGTH: 9
<212> TYPE: DNA
<213> ORGANISM: Artificial Sequence
<220> FEATURE:
<223> OTHER INFORMATION: Synthesized Translation Enhancer Element
      Oligonucleotide  M1-5 corresponding generally to TEE Consensus
      Motif 1

<400> SEQUENCE: 9 cggagcgaa                                                                9

<210> SEQ ID NO 10
<211> LENGTH: 9
<212> TYPE: DNA
<213> ORGANISM: Artificial Sequence
<220> FEATURE:
<223> OTHER INFORMATION: Synthesized Translation Enhancer Element
      Oligonucleotide  M1-6 corresponding generally to TEE Consensus
      Motif 1

<400> SEQUENCE: 10 cggagcgga                                                                9

<210> SEQ ID NO 11
<211> LENGTH: 9
<212> TYPE: DNA
<213> ORGANISM: Artificial Sequence
<220> FEATURE:
<223> OTHER INFORMATION: Synthesized Translation Enhancer Element
      Oligonucleotide M1-7 corresponding generally to TEE Consensus
      Motif 1

<400> SEQUENCE: 11 acgagagga                                                                9

<210> SEQ ID NO 12
<211> LENGTH: 9
<212> TYPE: DNA
<213> ORGANISM: Artificial sequence
<220> FEATURE:
<223> OTHER INFORMATION: Synthesized Translation Enhancer Element
      Oligonucleotide M1-8 corresponding generally to TEE Consensus
      Motif 1

<400> SEQUENCE: 12 acgagcgga                                                                9

<210> SEQ ID NO 13
<211> LENGTH: 10
<212> TYPE: DNA
<213> ORGANISM: Artificial Sequence
<220> FEATURE:
<223> OTHER INFORMATION: Synthesized Translation Enhancer Element
      Oligonucleotide M1-9 corresponding generally to TEE Consensus
      Motif 1

<400> SEQUENCE: 13
gacgagagga                                                              10

<210> SEQ ID NO 14
<211> LENGTH: 10
<212> TYPE: DNA
<213> ORGANISM: Artificial Sequence
<220> FEATURE:

```
<223> OTHER INFORMATION: Synthesized Translation Enhancer Element
      Oligonucleotide M1-10 corresponding generally to TEE Consensus
      Motif 1

<400> SEQUENCE: 14
gacgagagaa                                                              10

<210> SEQ ID NO 15
<211> LENGTH: 8
<212> TYPE: DNA
<213> ORGANISM: Artificial sequence
<220> FEATURE:
<223> OTHER INFORMATION: Synthesized Translation Enhancer Element
      Oligonucleotide M1-11 corresponding generally to TEE Consensus
      Motif 1

<400> SEQUENCE: 15 agcgagcg                                                                 8

<210> SEQ ID NO 16
<211> LENGTH: 9
<212> TYPE: DNA
<213> ORGANISM: Artificial Sequence
<220> FEATURE:
<223> OTHER INFORMATION: Synthesized Translation Enhancer Element
      Oligonucleotide M1-12 (1'3) corresponding generally to TEE
      Consensus Motif 1

<400> SEQUENCE: 16 aggagagga                                                                9

<210> SEQ ID NO 17
<211> LENGTH: 9
<212> TYPE: DNA
<213> ORGANISM: Artificial Sequence
<220> FEATURE:
<223> OTHER INFORMATION: Synthesized Translation Enhancer Element
      Oligonucleotide M-13 (5'1) corresponding generally to TEE
      Consensus Motif 1

<400> SEQUENCE: 17 gccgagaga                                                                9

<210> SEQ ID NO 18
<211> LENGTH: 9
<212> TYPE: DNA
<213> ORGANISM: Artificial Sequence
<220> FEATURE:
<223> OTHER INFORMATION: Synthesized Translation Enhancer Element
      Oligonucleotide M1-14 (5'3) corresponding generally to TEE
      Consensus Motif 1

<400> SEQUENCE: 18 cgagaggca                                                                9

<210> SEQ ID NO 19
<211> LENGTH: 9
<212> TYPE: DNA
<213> ORGANISM: Artificial sequence
<220> FEATURE:
<223> OTHER INFORMATION: Synthesized Translation Enhancer Element
      Oligonucleotide M1-15 (1'4) corresponding generally to TEE
      Consensus Motif 1

<400> SEQUENCE: 19 gagaggagc                                                                9
```

```
<210> SEQ ID NO 20
<211> LENGTH: 9
<212> TYPE: DNA
<213> ORGANISM: Artificial sequence
<220> FEATURE:
<223> OTHER INFORMATION: Synthesized Translation Enhancer Element
      Oligonucleotide M2-1 corresponding generally to TEE Consensus
      Motif 2

<400> SEQUENCE: 20 cgcggcgga                                                                 9

<210> SEQ ID NO 21
<211> LENGTH: 9
<212> TYPE: DNA
<213> ORGANISM: Artificial sequence
<220> FEATURE:
<223> OTHER INFORMATION: Synthesized Translation Enhancer Element
      Oligonucleotide M2-2 corresponding generally to TEE Consensus
      Motif 2

<400> SEQUENCE: 21 cgccgccgc                                                                 9

<210> SEQ ID NO 22
<211> LENGTH: 9
<212> TYPE: DNA
<213> ORGANISM: Artificial sequence
<220> FEATURE:
<223> OTHER INFORMATION: Synthesized Translation Enhancer Element
      Oligonucleotide M2-3 corresponding generally to TEE Consensus
      Motif 2

<400> SEQUENCE: 22 gcggctgaa                                                                 9

<210> SEQ ID NO 23
<211> LENGTH: 9
<212> TYPE: DNA
<213> ORGANISM: Artificial Sequence
<220> FEATURE:
<223> OTHER INFORMATION: Synthesized Translation Enhancer Element
      Oligonucleotide M2-4 corresponding generally to TEE Consensus
      Motif 2

<400> SEQUENCE: 23 ccggctgaa                                                                 9

<210> SEQ ID NO 24
<211> LENGTH: 10
<212> TYPE: DNA
<213> ORGANISM: Artificial sequence
<220> FEATURE:
<223> OTHER INFORMATION: Synthesized Translation Enhancer Element
      Oligonucleotide M2-5 corresponding generally to TEE Consensus
      Motif 2

<400> SEQUENCE: 24
cgccgctgaa                                                               10

<210> SEQ ID NO 25
<211> LENGTH: 10
<212> TYPE: DNA
<213> ORGANISM: Artificial sequence
<220> FEATURE:
<223> OTHER INFORMATION: Synthesized Translation Enhancer Element
      Oligonucleotide M2-6 corresponding generally to TEE Consensus
      Motif 2
```

```
<400> SEQUENCE: 25
cgccgcggaa                                                            10

<210> SEQ ID NO 26
<211> LENGTH: 10
<212> TYPE: DNA
<213> ORGANISM: Artificial sequence
<220> FEATURE:
<223> OTHER INFORMATION: Synthesized Translation Enhancer Element
      Oligonucleotide M2-7 corresponding generally to TEE Consensus
      Motif 2

<400> SEQUENCE: 26
cgccgccgaa                                                            10

<210> SEQ ID NO 27
<211> LENGTH: 9
<212> TYPE: DNA
<213> ORGANISM: Artificial sequence
<220> FEATURE:
<223> OTHER INFORMATION: Synthesized Translation Enhancer Element
      Oligonucleotide M2-8 corresponding generally to TEE Consensus
      Motif 2

<400> SEQUENCE: 27 cccgcggaa                                                              9

<210> SEQ ID NO 28
<211> LENGTH: 9
<212> TYPE: DNA
<213> ORGANISM: Artificial sequence
<220> FEATURE:
<223> OTHER INFORMATION: Synthesized Translation Enhancer Element
      Oligonucleotide M2-9 corresponding generally to TEE Consensus
      Motif 2

<400> SEQUENCE: 28 cccgccgaa                                                              9

<210> SEQ ID NO 29
<211> LENGTH: 9
<212> TYPE: DNA
<213> ORGANISM: Artificial sequence
<220> FEATURE:
<223> OTHER INFORMATION: Synthesized Translation Enhancer Element
      Oligonucleotide M2-10 corresponding generally to TEE Consensus
      Motif 2

<400> SEQUENCE: 29 cccgctgaa                                                              9

<210> SEQ ID NO 30
<211> LENGTH: 9
<212> TYPE: DNA
<213> ORGANISM: Artificial Sequence
<220> FEATURE:
<223> OTHER INFORMATION: Synthesized Translation Enhancer Element
      Oligonucleotide M2-11 (G3) corresponding generally to TEE
      Consensus Motif 2

<400> SEQUENCE: 30 cccggcgga                                                              9

<210> SEQ ID NO 31
<211> LENGTH: 9
<212> TYPE: DNA
<213> ORGANISM: Artificial sequence
```

```
<220> FEATURE:
<223> OTHER INFORMATION: Synthesized Translation Enhancer Element
      Oligonucleotide M2-12 (4'3) corresponding generally to TEE
      Consensus Motif 2

<400> SEQUENCE: 31 cgcggctga                                                                      9

<210> SEQ ID NO 32
<211> LENGTH: 9
<212> TYPE: DNA
<213> ORGANISM: Artificial sequence
<220> FEATURE:
<223> OTHER INFORMATION: Synthesized Translation Enhancer Element
      Oligonucleotide M2-13 (4'5) corresponding generally to TEE
      Consensus Motif 2

<400> SEQUENCE: 32 cggctgcta                                                                      9

<210> SEQ ID NO 33
<211> LENGTH: 9
<212> TYPE: DNA
<213> ORGANISM: Artificial sequence
<220> FEATURE:
<223> OTHER INFORMATION: Synthesized Translation Enhancer Element
      Oligonucleotide M2-14 (G2) corresponding generally to TEE
      Consensus Motif 2

<400> SEQUENCE: 33 cccggcgga                                                                      9

<210> SEQ ID NO 34
<211> LENGTH: 10
<212> TYPE: DNA
<213> ORGANISM: Artificial sequence
<220> FEATURE:
<223> OTHER INFORMATION: Synthesized Translation Enhancer Element
      Oligonucleotide M2-15 (G12) corresponding generally to TEE
      Consensus Motif 2

<400> SEQUENCE: 34
agccgccgca                                                                    10

<210> SEQ ID NO 35
<211> LENGTH: 10
<212> TYPE: DNA
<213> ORGANISM: Artificial sequence
<220> FEATURE:
<223> OTHER INFORMATION: Synthesized Translation Enhancer Element
      Oligonucleotide M2-16 (G11) corresponding generally to TEE
      Consensus Motif 2

<400> SEQUENCE: 35
acgccgccga                                                                    10
```